United States Patent
Love et al.

(10) Patent No.: US 11,690,762 B2
(45) Date of Patent: Jul. 4, 2023

(54) METAL-DETECTABLE LENS ASSEMBLIES AND PROTECTIVE EYEWEAR INCLUDING SAME

(71) Applicant: Gateway Safety, Inc., Cleveland, OH (US)

(72) Inventors: Michael D. Love, Avon, OH (US); Bonnie K. San, Berea, OH (US)

(73) Assignee: Gateway Safety, Inc., Cleveland, OH (US)

( * ) Notice: Subject to any disclaimer, the term of this patent is extended or adjusted under 35 U.S.C. 154(b) by 0 days.

(21) Appl. No.: 17/014,571

(22) Filed: Sep. 8, 2020

(65) Prior Publication Data

US 2021/0069019 A1    Mar. 11, 2021

Related U.S. Application Data

(60) Provisional application No. 62/897,890, filed on Sep. 9, 2019.

(51) Int. Cl.
   *A61F 9/02*        (2006.01)

(52) U.S. Cl.
   CPC ............... *A61F 9/029* (2013.01); *A61F 9/02* (2013.01)

(58) Field of Classification Search
   CPC ............ A61F 9/02; A61F 9/029; G02C 5/001
   See application file for complete search history.

(56) References Cited

U.S. PATENT DOCUMENTS

| | | | |
|---|---|---|---|
| 4,942,629 A | 7/1990 | Stadlmann | |
| 5,018,223 A | 5/1991 | Gregory | |
| 5,189,447 A * | 2/1993 | Oleson | G02C 5/146 |
| | | | 2/448 |
| 5,319,397 A | 6/1994 | Ryden | |
| 6,010,220 A | 1/2000 | Smarto | |
| 6,213,602 B1 | 4/2001 | Smarto | |
| 6,769,767 B2 | 8/2004 | Swab | |
| 6,783,238 B1 | 8/2004 | Stepper | |
| 6,824,265 B1 | 11/2004 | Harper | |
| 7,004,581 B2 | 2/2006 | Landers | |
| 7,104,645 B2 | 9/2006 | Pilat, Jr. | |
| 7,241,007 B2 | 7/2007 | Cody | |
| D548,266 S | 8/2007 | Landers | |
| 7,648,234 B2 | 1/2010 | Welchel et al. | |
| 7,850,301 B2 | 12/2010 | Dichiara | |
| 7,967,435 B1 * | 6/2011 | Seeto | G01V 15/00 |
| | | | 351/159.57 |
| 7,988,282 B2 | 8/2011 | Laustsen et al. | |
| 8,342,679 B2 * | 1/2013 | Seeto | G02C 5/008 |
| | | | 351/41 |

(Continued)

FOREIGN PATENT DOCUMENTS

| CN | 206757230 U | 12/2017 |
|---|---|---|
| CN | 209590443 U | 11/2019 |

(Continued)

*Primary Examiner* — F Griffin Hall
(74) *Attorney, Agent, or Firm* — Matthew P. Dugan

(57) ABSTRACT

Protective eyewear lens assemblies include one or more metal-detectable components and a lens body. The lens body is formed from a polymeric material and the one or more metal-detectable component are permanently encapsulated on, along or within the lens body. Protective eyewear including such lens assemblies and methods of manufacture are also included.

20 Claims, 16 Drawing Sheets

(56) References Cited

U.S. PATENT DOCUMENTS

| | | | |
|---|---|---|---|
| 8,641,188 B2* | 2/2014 | DiChiara | G02C 1/04 |
| | | | 351/86 |
| 9,229,248 B2 | 1/2016 | Kokonaski et al. | |
| 9,289,623 B2 | 3/2016 | Pugh et al. | |
| 9,366,882 B2 | 6/2016 | Iurilli | |
| 2007/0298242 A1* | 12/2007 | Huo | G02C 7/108 |
| | | | 428/323 |
| 2013/0235328 A1 | 9/2013 | Cauvet et al. | |
| 2013/0271722 A1 | 10/2013 | Dichiara | |
| 2013/0342807 A1 | 12/2013 | Blum et al. | |
| 2016/0204839 A1 | 7/2016 | Liu et al. | |
| 2017/0068110 A1 | 3/2017 | Ho | |
| 2021/0173232 A1 | 6/2021 | Wang et al. | |

FOREIGN PATENT DOCUMENTS

| | | | |
|---|---|---|---|
| CN | 111273461 A | 6/2020 | |
| FR | 1081963 A | 12/1954 | |
| GB | 1183487 A | 3/1970 | |

* cited by examiner

METAL-DETECTABLE LENS ASSEMBLIES AND PROTECTIVE EYEWEAR INCLUDING SAME

This application claims the benefit of priority to U.S. Provisional Patent Application Ser. No. 62/897,890, filed on Sep. 9, 2019, the contents of which is hereby incorporated herein by reference in its entirety.

BACKGROUND

The subject matter of the present disclosure broadly relates to the art of personal protective equipment and, more particularly, to polymeric lens assemblies with one or more portions that include detectable quantities of metal as well as protective eyewear including one or more of such polymeric lens assemblies and methods of manufacturing polymeric lens assemblies and protective eyewear.

It is widely recognized and understood that manufacturing and agricultural facilities of a variety of types and kinds commonly utilize processing and/or conveying equipment during the manufacture of products. In some cases, one or more of these processing and/or conveying lines may be open to an open atmosphere, such as the interior of a building. As a non-limiting example, facilities that process meat or other foods often utilize long conveyor belts that have workers positioned along one or both sides of the conveyor belts performing various tasks in connection with the processing of the meat or other food products. In these and other cases, it may be possible for foreign objects and/or materials to inadvertently or otherwise enter the stream of food items being processed. To minimize the possibility of such foreign objects and/or materials from being incorporated into the final product, facilities commonly employ equipment and techniques to sense and thereby identify foreign material. As a non-limiting example, food items may be passed through one or more metal detectors to aid in identifying any foreign objects or materials at various stages throughout the process.

It has been recognized, however, that personal protective equipment is often manufactured from plastic materials, which are typically undetectable by conventional detection systems and/or processes. In some cases, one or more metal components have been added or otherwise assembled into personal protective equipment thereby rendering those products potentially detectable. To be suitable for use, however, lenses of protective eyewear are optically clear in at least one area so that the wearer can see through the lens of the protective eyewear. As such, known constructions of protective eyewear have relied upon metallic fasteners and/or rigid structural features made from metal to permit detection of the protective eyewear. However, in cases in which conventional protective eyewear is inadvertently broken and enters the stream of food items in one or more pieces, it may be possible for some of the pieces to pass undetected through any equipment or systems intended to identify such foreign objects or materials.

Accordingly, it is believed desirable to develop detectable lenses as well as protective eyewear including one or more of such lenses to aid in addressing the foregoing and/or other areas for improvement associated with detection of foreign objects and/or materials in connection with known manufacturing processes.

BRIEF SUMMARY

One example of a protective eyewear lens assembly in accordance with the subject matter of the present disclosure can include a lens body at least partially formed from a first quantity of polymeric material. The lens body can have a width and can extend widthwise between a first end and a second end opposite the first end. The lens body can include a surface portion with a first hinge connection portion disposed along the first end and a second hinge connection portion disposed along the second end. A metal-detectable component can be supported along the surface portion of the lens body with the metal-detectable component permanently encased on the lens body by a second quantity of polymeric material.

One example of a protective eyewear assembly in accordance with the subject matter of the present disclosure can include a lens assembly that can include a lens body and a metal-detectable component. The lens body can be at least partially formed from a first quantity of polymeric material. The lens body can have a width and can extend widthwise between a first end and a second end opposite the first end. The lens body can include a surface portion with a first hinge connection portion disposed along the first end and a second hinge connection portion disposed along the second end. The metal-detectable component can be supported along the surface portion of the lens body with the metal-detectable component permanently encased along the lens body by a second quantity of polymeric material. A first temple can be pivotally attached to the first hinge connection of the lens body. A second temple can be pivotally attached to the second hinge connection of the lens body.

One example of a method of manufacturing a protective eyewear lens assembly in accordance with the subject matter of the present disclosure can include providing a lens body that can be at least partially formed from a first quantity of polymeric material. The lens body can have a width and can extend widthwise between a first end and a second end opposite the first end. The lens body can include a surface portion with a first hinge connection portion disposed along the first end and a second hinge connection portion disposed along the second end. The method can also include providing a metal-detectable component, and positioning the metal-detectable component along the surface portion of the lens body. The method can further include permanently encasing the metal-detectable component along the surface portion of the lens body with a second quantity of polymeric material.

DETAILED DESCRIPTION

Figure 1:
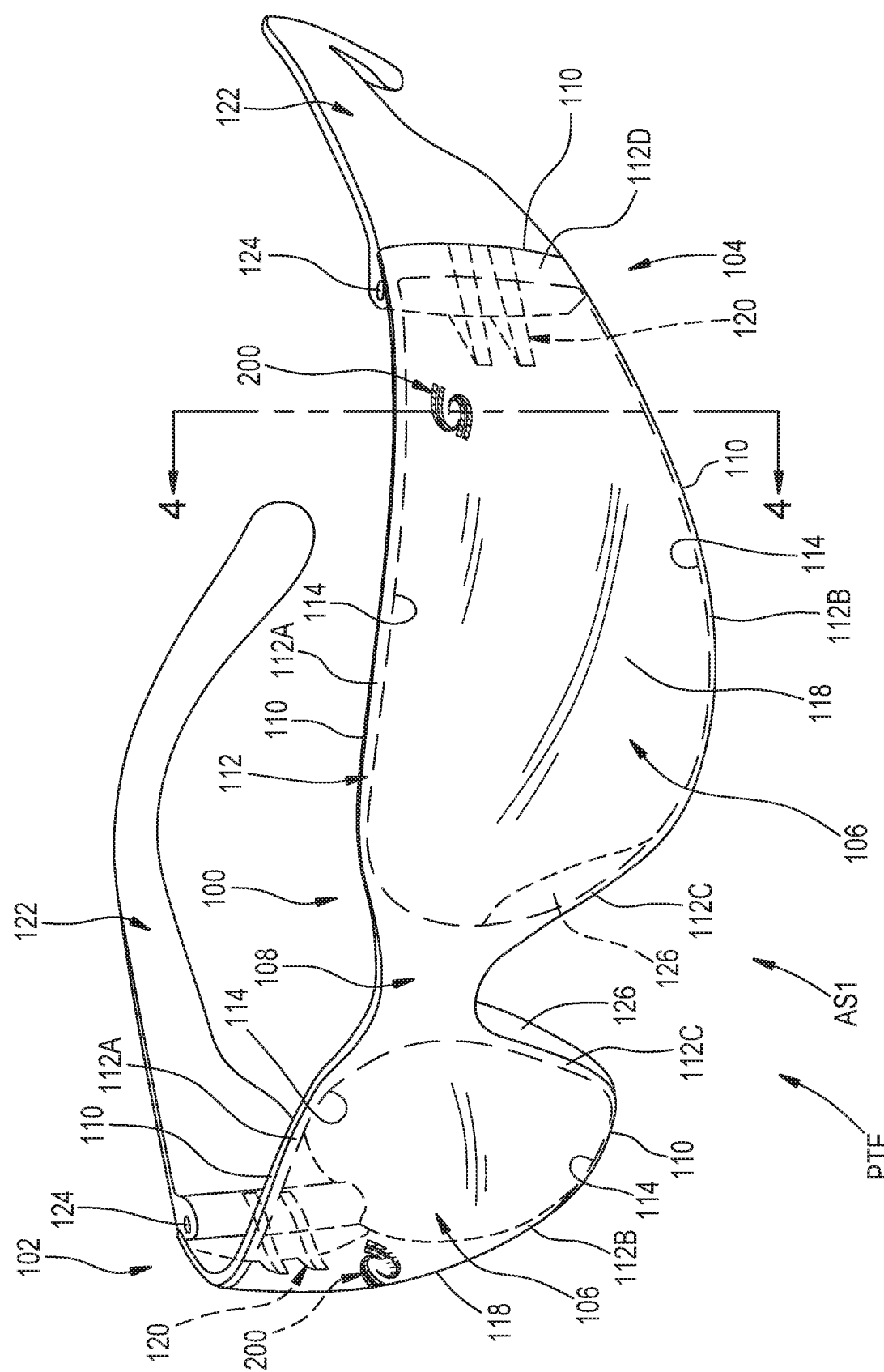
FIG. 1 is a top perspective view of one example of protective eyewear with a lens assembly in accordance with the subject matter of the present disclosure.

Turning now to the drawings, it is to be understood that the showings are for purposes of illustrating examples of the subject matter of the present disclosure and are not intended to be limiting. Additionally, it will be appreciated that the drawings are not to scale and that portions of certain features and/or elements may be exaggerated for purposes of clarity and/or ease of understanding.

In some cases, protective eyewear in accordance with the subject matter of the present disclosure can include two lens assemblies with one lens assembly supported on each side of the wearer's nose and in front of each of the wearer's eyes when the protective eyewear is being worn. In other cases, protective eyewear in accordance with the subject matter of the present disclosure can include a single lens assembly that is supported across the wearer's nose with a different portion of the lens assembly in front of each of the wearer's eyes when the protective eyewear is being worn. It is to be appreciated and distinctly understood that, while protective eyewear in accordance with the subject matter of the present disclosure are shown and described herein with reference to constructions including a single lens assembly, the subject matter of the present disclosure is equally applicable to protective eyewear including two lens assemblies and that the constructions and methods shown and described herein are merely exemplary and not intended to be limiting.

FIGS. 1-3 and 6-9 illustrate examples of protective eyewear PTE that includes at least one protective eyewear lens assembly in accordance with the subject matter of the present disclosure. The at least one lens assembly can include one or more lens components or bodies 100 that are at least partially formed from a polymeric material, such as an optically-transparent polycarbonate material, for example. Lens bodies 100 preferably include one or more optically-transparent portions that are positioned such that a wearer can look through the one or more optically-transparent portions in an otherwise typical fashion when the protective eyewear are in use. So, when in use in a conventional manner, protective eyewear PTE will be oriented such that lens body 100 has a top and a bottom spaced apart from one another in a heightwise direction with lens body ends 102 and 104 that are spaced apart from one another in a widthwise direction oriented transverse to the heightwise direction.

In the arrangements shown in FIGS. 1-15, lens body 100 includes optically-transparent portions 106 with a bridge portion 108 disposed therebetween. Lens body 100 also includes an outer peripheral edge 110. In some cases, optically-transparent portions 102 can at least partially define the outer peripheral edge. In other cases, lens body 100 can include a body periphery portion that at least partially defines the outer peripheral edge of the lens body. In some cases, the body periphery portion can form a substantially contiguous border or band around lens body 100. In other cases, the body periphery portion can include two or more separate or discrete segments. In either case and as non-limiting examples, lens body 100 can include a body periphery portion 112 that can include one or more segments 112A of body periphery portion 112 disposed along top or upper portions of the outer peripheral edge. Body periphery portion 112 can also include one or more segments 112B disposed along bottom or lower portions of the outer peripheral edge. Body periphery portion 112 can further include one or more segments 112C disposed along inward portions of the outer peripheral edge, such as may be adjacent bridge portion 108, for example. Body periphery portion 112 can also include one or more segments 112D disposed outward of segments 112C in the widthwise direction, such as along ends 102 and 104, for example.

Optically-transparent portions 106 can be disposed inward of outer peripheral edge 110 and/or body periphery portion 112. In some cases, body periphery portion 112 and/or any one or more of segments 112A-D thereof can include or otherwise be at least partially formed from a material that is separate and distinct from the material of optically-transparent portions 106 and/or bridge portion 108. In other cases, body periphery portion 112 can be unitarily formed with optically-transparent portions 106 and/or bridge portion 108 from a common polymeric material. In such cases, body periphery portion 112 can, optionally, be frosted, colored, opaque or otherwise less optically-transparent than portions 106 and/or 108. As such, it will be appreciated that in any construction in accordance with the subject matter of the present disclosure a visible demarcation line may, in some cases, be present where optically-transparent portions 106 transition into body periphery portion 112 (and/or any one or more of segments 112A-D thereof), such as is represented in FIGS. 1-9 by intersection or dashed line 114, for example. In some cases, body periphery portion 112 can include an additional volume of material, such as may be suitable for at least partially embedding, encasing and/or otherwise capturing one or metal-detectable components on, along and/or within lens body 100.

It will be appreciated that lens bodies 100 can include one or more inside surface portions 116 facing toward the user when protective eyewear PTE is being worn and one or more outside surface portions 118 facing away from the user when the protective eyewear is being worn. Ends 102 and 104 are disposed adjacent or otherwise along optically-transparent portion 106 in a direction outboard of or otherwise spaced outward of bridge portion 108. It will be appreciated that the lens body ends are spaced apart from one another in the widthwise direction with bridge portion 108 disposed therebetween such that one of optically-transparent portions 106 is disposed between the bridge portion and one of lens body ends 102 and/or 104. Additionally, lens bodies 100 can include a pivot or hinge connection 120 disposed on or along body ends 102 and/or 104, such as on or along segments 112D of body periphery portion 112, for example. In a preferred arrangement, hinge connections 120 are unitarily formed from a common polymeric material with optically-transparent portions 106, bridge portion 108 and/or body periphery portion 112.

Protective eyewear PTE can also include any suitable number of one or more additional features and/or components. As a non-limiting example, protective eyewear PTE can include temples 122 secured in a suitable manner on or along opposing ends 102 and 104 of lens body 100. As one non-limiting example, temples 122 can be pivotally connected or otherwise secured to hinge connections 120 of lens body 100 using a suitable fastener 124, such as a pin, screw, rivet, or other connection, for example. In some cases, such a pin, screw, rivet, or other fastener may be formed from a metal material. As another example, protective eyewear PTE can, in some cases, include one or more nose pads 126 disposed below bridge portion 104 to support protective eyewear PTE on the nose of a wearer in an otherwise conventional fashion. In some cases, nose pads 126 can be provided separately from lens body 100 and can be secured thereto in a suitable manner. In other cases, the nose pads can be unitarily formed from a common polymeric material with optically-transparent portions 106, bridge portion 108 and/or body periphery portion 112.

In accordance with the subject matter of the present disclosure, a lens assembly of protective eyewear PTE also includes one or more metal-detectable components (which are also referred to herein as "metal-detectable inserts") disposed along the lens body (or bodies). In a preferred arrangement, one or more of the detectable components are at least partially embedded, encased and/or otherwise captured on, along and/or within the lens body (or bodies). Additionally, in a preferred arrangement, one or more of the detectable components can be of a size, shape and/or configuration that provides negligible strength, stiffening and/or other structural support to the lens body (or bodies). Furthermore, the one or more metal-detectable components are preferably permanently attached (i.e., inseparable without damage, destruction or material alteration of at least one of the component parts) to the lens body (or bodies).

Figure 4:
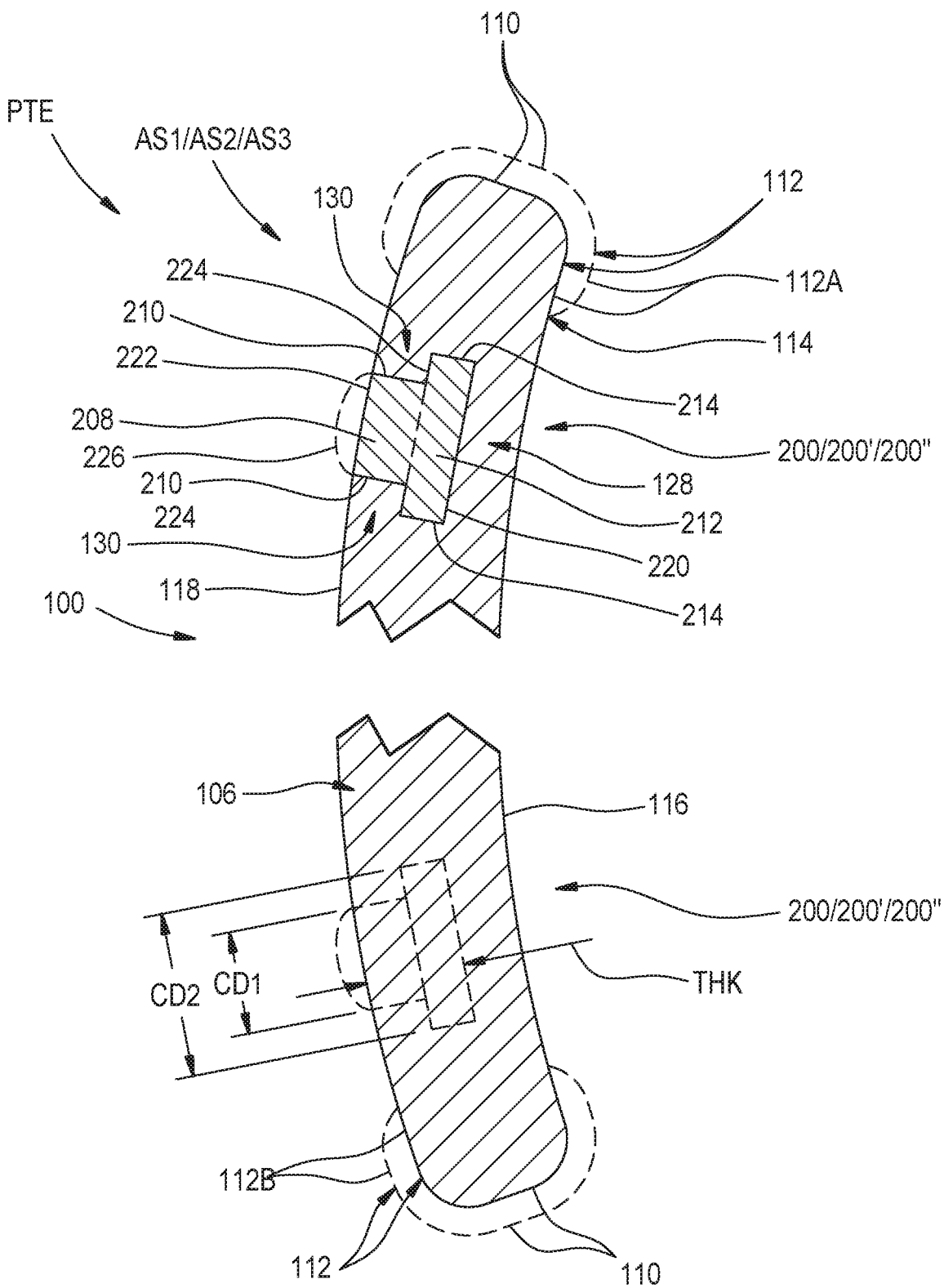
FIG. 4 is a cross-sectional side view of the exemplary lens assemblies shown in FIGS. 1-3 taken from along lines 4-4 therein.
Figure 5:
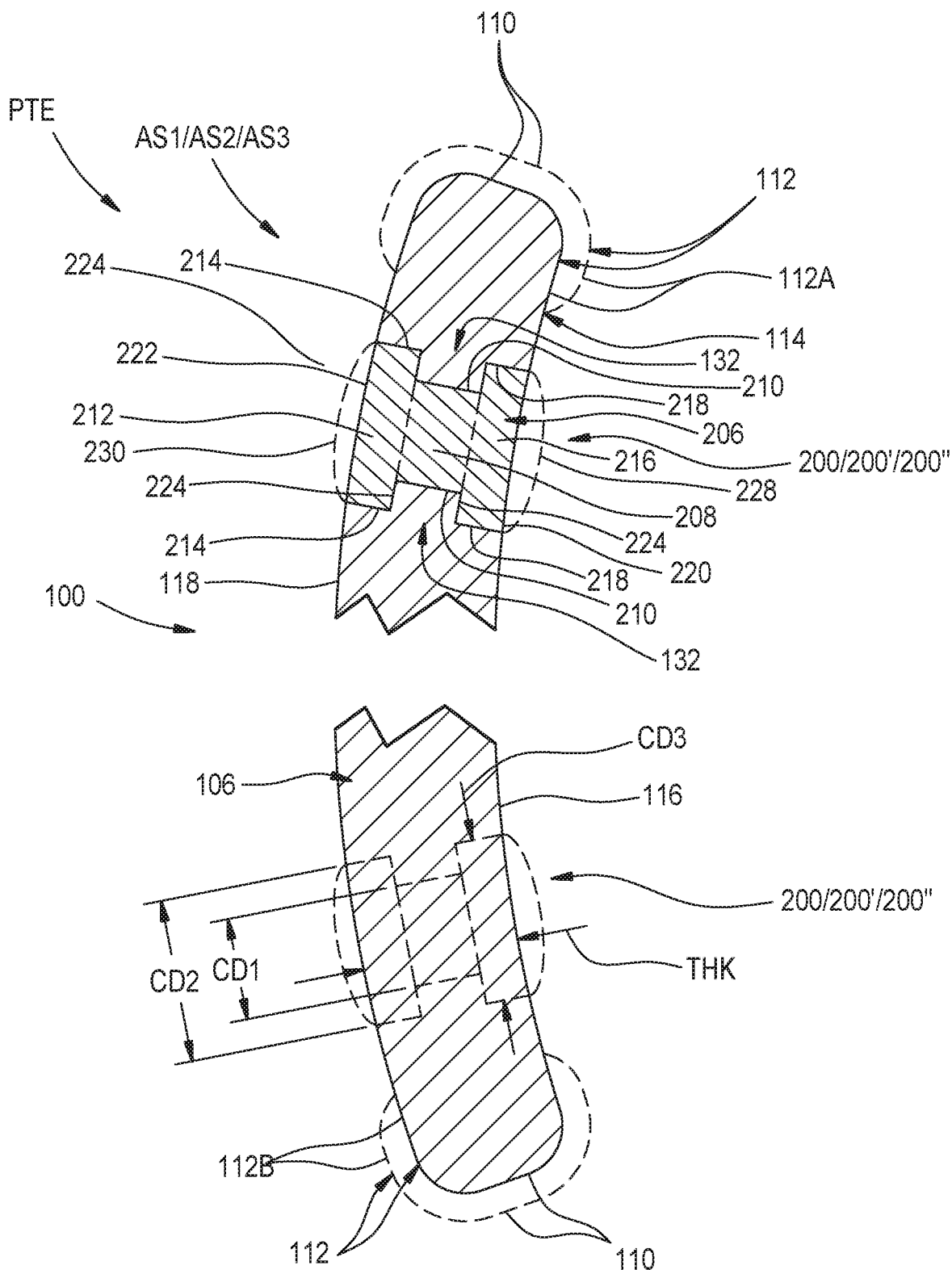
FIG. 5 is a cross-sectional side view of an alternate construction of the lens assemblies in FIGS. 1-4.

As one non-limiting example, a protective eyewear lens assembly AS1 in accordance with the subject matter of the present disclosure is shown in FIGS. 1, 4 and 5 as including lens body 100, as shown and described above, and one or more metal-detectable components 200 that are at least partially embedded, encased and/or otherwise captured on, along and/or within lens body 100. That is, metal-detectable component 200 is, preferably, at least partially embedded, encased and/or otherwise captured on, along and/or within the constituent material of lens body such that a surface (or surface portion) of each of the detectable components is exposed along the inside surface, the outside surface or both the inside and outside surfaces of lens body 100. It will be appreciated that detectable components 200 can be of any suitable size, shape and/or configuration, such as may include any one or more of logos, symbols, geometric elements and/or characters. In a preferred arrangement, at least one of metal-detectable components 200 is included on or along each side (in the widthwise direction) of lens body 100 such that upon being separated into two pieces, such due to a disconnection along bridge portion 108, for example, each of the two pieces will include at least one of metal-detectable component 200. It will be appreciated that metal-detectable components can be formed from any suitable material or combination of materials, such as one or more materials that can be detected or are detectable using conventional systems, equipment and/or techniques for identifying foreign material in manufacturing and/or food production processes (e.g., magnetically-detectable and/or otherwise metal-detectable). As non-limiting examples, detectable components 200 could be at least partially formed from a metal material and/or a metal-infused polymeric material.

Figure 2:
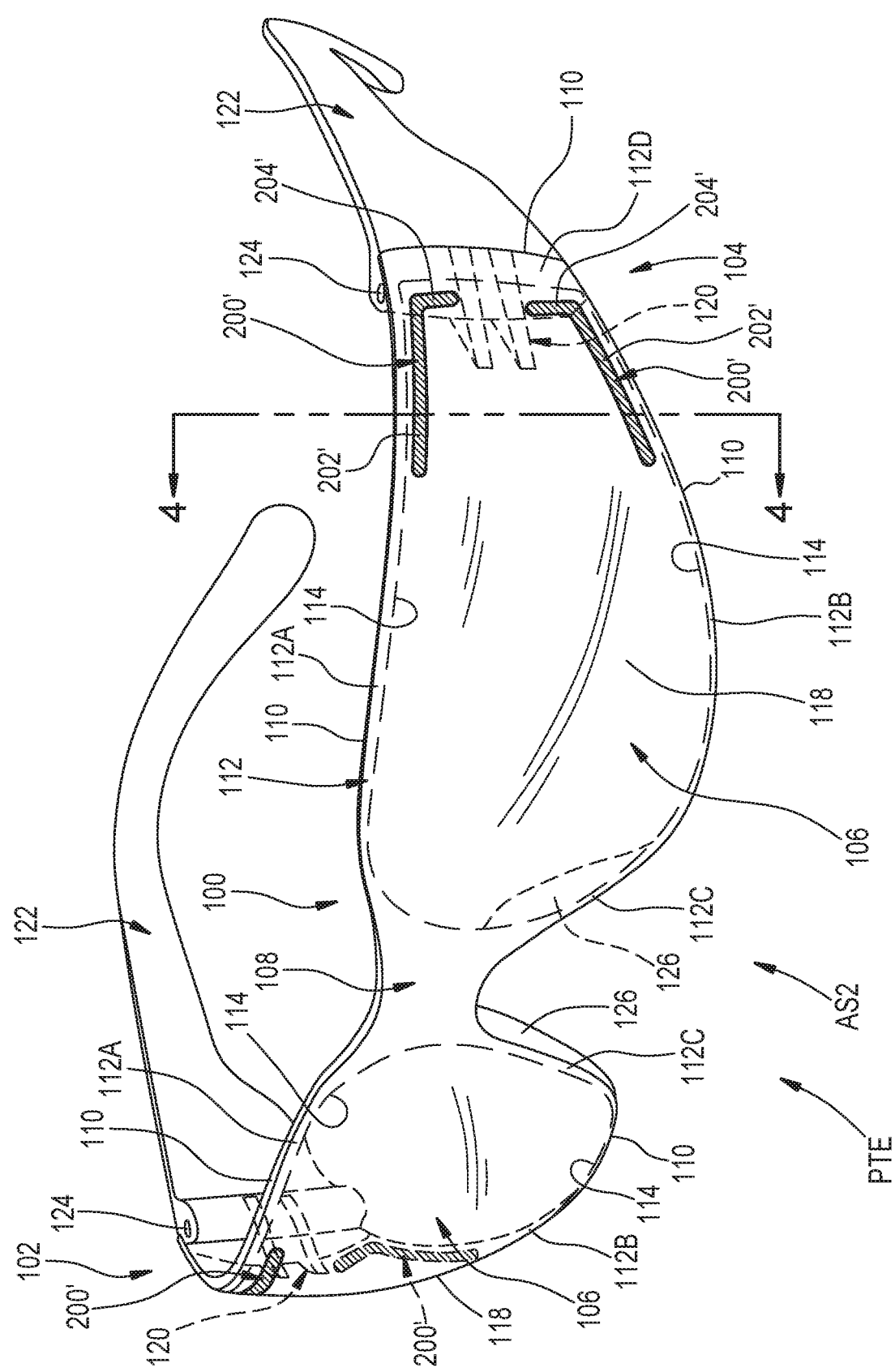
FIG. 2 is a top perspective view of another example of protective eyewear with a lens assembly in accordance with the subject matter of the present disclosure.

As another non-limiting example, a protective eyewear lens assembly AS2 in accordance with the subject matter of the present disclosure is shown in FIGS. 2, 4 and 5 as including lens body 100, as shown and described above, and one or more metal-detectable components 200' that are at least partially embedded, encased and/or otherwise captured on, along and/or within lens body 100. Metal-detectable components 200' are at least partially embedded, encased and/or otherwise captured on, along and/or within the lens body such that a surface (or surface portion) of each of the detectable components is exposed along the inside surface, the outside surface or both the inside and outside surfaces of lens body 100. Metal-detectable components 200' differ from metal-detectable components 200, shown and described in connection with FIG. 1, in that metal-detectable components 200' include an elongated length of metal-detectable material (e.g., a metal material and/or a metal-infused polymeric material) with at least a first elongated portion 202' and a second elongated portion 204' oriented transverse to first elongated portion 202'. In a preferred arrangement, first elongated portion 202' can extend adjacent and/or otherwise along a first part of body periphery portion 112 (e.g., one of segments 112A and/or 112B). Additionally, or in the alternative, second elongated portion 204' can extend adjacent and/or otherwise along a part of body periphery portion 112 (e.g., one of segments 112C and/or 112D). In a preferred arrangement, at least one of metal-detectable components 200' is included on or along each side (in the widthwise direction) of lens body 100 such that upon being separated into two pieces, such due to a disconnection along bridge portion 108, for example, each of the two pieces will include at least one of metal-detectable component 200'. In the exemplary arrangement shown in FIG. 2, lens assembly AS2 includes four metal-detectable components 200' with two of the metal detectable components disposed along each side of bridge portion 108 in the widthwise direction toward outward each of segments 112D. Additionally, two of metal detectable components 200' are disposed along the upper portions of outer peripheral edge 110 (e.g., along segments 112A) and two of metal detectable components 200' are disposed along the lower portions of outer peripheral edge 110 (e.g., along segments 112B). It will be appreciated, however, that other configurations and/or arrangements can be used without departing from the subject matter of the present disclosure.

Figure 3:
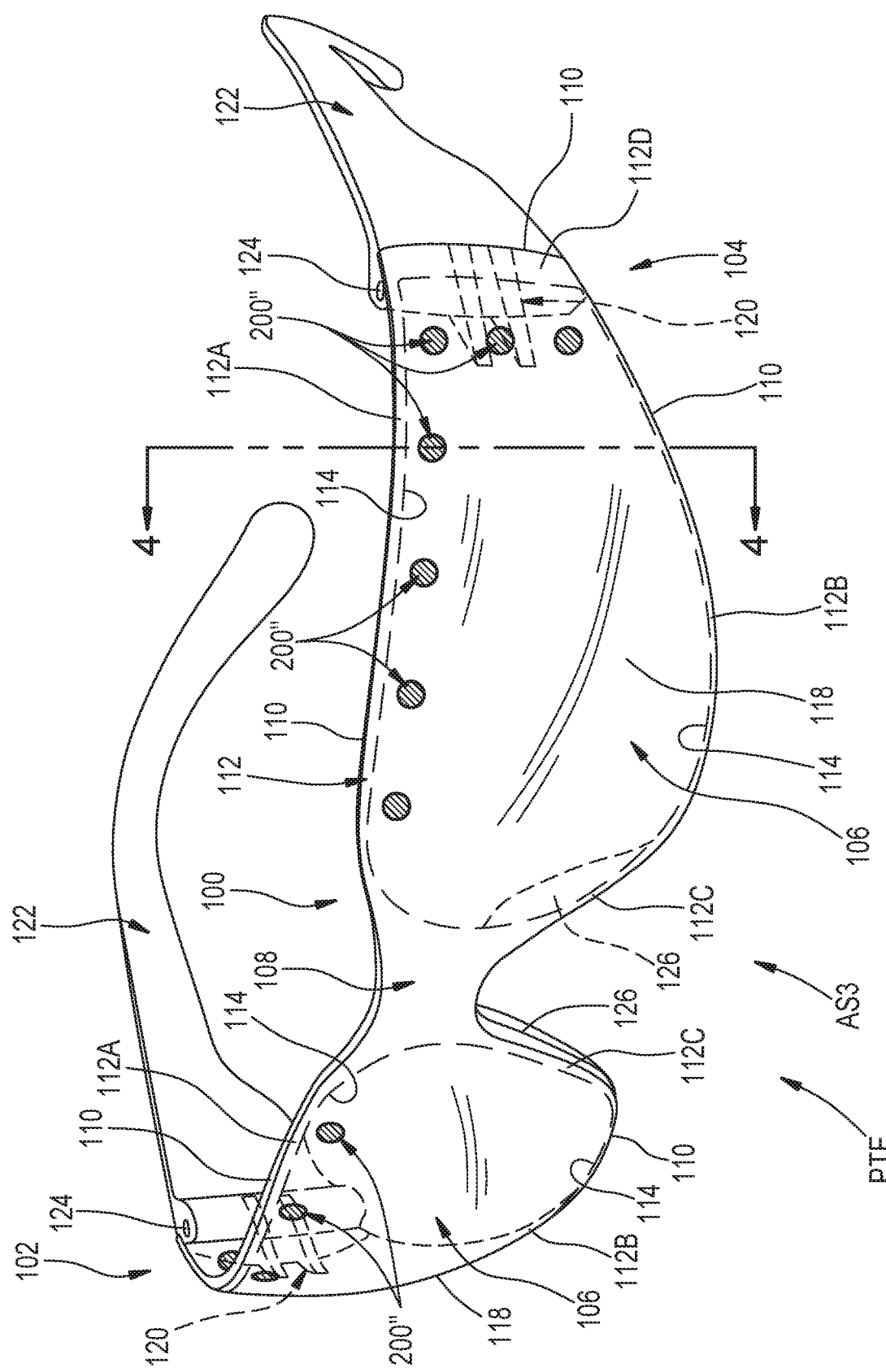
FIG. 3 is a top perspective view of a further example of protective eyewear with a lens assembly in accordance with the subject matter of the present disclosure.

As a further non-limiting example, a protective eyewear lens assembly AS3 in accordance with the subject matter of the present disclosure is shown in FIGS. 3-5 as including lens body 100, as shown and described above, and one or more metal-detectable components 200" that are at least partially embedded, encased and/or otherwise captured on, along and/or within lens body 100. Metal-detectable components 200" are at least partially embedded, encased and/or otherwise captured on, along and/or within the lens body such that a surface (or surface portion) of each of the detectable components is exposed along the inside surface, the outside surface or both the inside and outside surfaces of lens body 100. Metal-detectable components 200" differ from metal-detectable components 200, shown and described in connection with FIG. 1, and from metal-detectable components 200', shown and described in connection with FIG. 2, in that metal-detectable components 200" include a plurality of metal-detectable material (e.g., a metal material and/or a metal-infused polymeric material) that are spaced apart from one another along a common part of body periphery portion 112 (e.g., along at least one of segments 112A, 112B, 112C and/or 112D). As one non-limiting example, lens assembly AS3 can include three (3) or more metal-detectable components 200 disposed in spaced relation to one another on or along a common part of body periphery portion 112. In a preferred arrangement, a plurality of metal-detectable components 200" are included on or along each side (in the widthwise direction) of lens body 100 such that upon being separated into two pieces, such due to a disconnection along bridge portion 108, for example, each of the two pieces will include two or more metal-detectable components 200". In the exemplary arrangement shown in FIG. 5, lens assembly AS3 includes fourteen (14) metal-detectable components 200" with seven (7) of the metal detectable components disposed along each side of bridge portion 108 in the widthwise direction and with two or more of the metal detectable components positioned along segments 112A and 112D. It will be appreciated, however, that other configurations and/or arrangements can be used without departing from the subject matter of the present disclosure.

With reference, now, to FIGS. 4 and 5, metal-detectable components 200, 200' and/or 200" can include a component body 206 that is at least partially formed from a magnetically-detectable and/or otherwise metal-detectable material (e.g., a metal material and/or a metal-infused polymeric material). In addition to the arrangement and/or configuration of metal-detectable components 200, 200' and/or 200", component bodies 206 thereof are configured to be at least partially embedded, encased and/or otherwise captured on, along and/or within lens body 100 such that the lens body and one or more metal-detectable components are permanently attached (i.e., inseparable without damage, destruction or material alteration of at least one of the component parts) to one another. Component bodies 206 have a cross-sectional shape with a thickness extending through lens body 100 in a direction transverse to the heightwise and widthwise directions, as is represented in FIGS. 4 and 5 by reference dimension THK. Component bodies 206 also include a body portion 208 with a cross-sectional dimension CD1 between side surface portions 210 that face away from one another. Component bodies 206 can also include a body portion 212 with a cross-sectional dimension CD2 between side surface portions 214 that face away from one another with cross-sectional dimension CD2 being greater than cross-sectional dimension CD1 (e.g., an approximately T-shaped configuration). As shown in FIG. 5, component bodies 206 can, in some cases, include a body portion 216 that is disposed along body portion 208 opposite body portion 212 (e.g., an approximately H-shaped configuration). Body portion 216 extends between side surface portions 218 that face away from one another with a cross-sectional dimension CD3 that is greater than cross-sectional dimension CD1. In some cases, cross-sectional dimensions CD2 and CD3 can have an approximately common size or value.

Component bodies 206 also include an inside surface portion 220 oriented toward inside surface portion 116 of lens body 100. Component bodies 206 can further include an outside surface portion 222 oriented toward outside surface portion 118 of the lens body. Additionally, component bodies 206 can include one or more intermediate surface portions 224 disposed between inside surface portion 220 and outside surface portion 222 (i.e., in the thickness direction). It will be appreciated that intermediate surface portions 224 in FIG. 4 are due, at least in part, to the difference between cross-sectional dimensions CD1 and CD2 with intermediate surface portions 224 in FIG. 4 facing away from inside surface portion 116 of lens body 100. Intermediate surface portions 224 in FIG. 5 are due, at least in part, to the difference between cross-sectional dimension CD1 and cross-sectional dimensions CD2 and CD3 with intermediate surface portions 224 in FIG. 5 facing toward one another such that a space or channel (not numbered) is formed therebetween that is disposed inwardly of inside and outside surface portions 220 and 222 in the thickness direction. Furthermore, it will be appreciated that the intermediate surface portions shown in FIG. 5 are approximately the same size and shape due, at least in part, to the common differences between cross-sectional dimension CD1 and cross-sectional dimensions CD2 and CD3. In some cases, however, intermediate surface portions of different sizes and/or shapes can be used. Further still, in some two or more separate intermediate surface portions can extend at least partially along the component body (e.g., one above and one below body portion 208 in FIG. 4). In other cases, an intermediate surface portion can cover a substantially-contiguous area that extends along and/or around body portion 208.

As discussed above, metal-detectable components are at least partially embedded, encased and/or otherwise captured on, along and/or within the lens body (or bodies) such that the metal-detectable components are permanently attached (i.e., inseparable without damage, destruction or material alteration of at least one of the component parts) to the lens body. In the arrangement shown in FIG. 4, outside surface portion 222 of component body 206 is exposed on or along outside surface portion 118 of lens body 100. In some cases, outside surface portion 222 can have a shape and/or contour that approximately matches that of outside surface portion 118 of lens body 100. In other cases, outside surface portion 222 of component body 206 can be approximately planar, recessed into and/or projecting outwardly beyond outside surface portions 118, such as is collectively represented in FIG. 4 by dashed lines 226. Additionally, inside surface portion 220 of component body 206 in FIG. 4 is disposed between the inside and outside surface portions of lens body 100. In such an arrangement, a portion 128 of lens body 100 is disposed between inside surface portion 116 and inside surface portion 220 and a portion 130 of lens body is disposed between intermediate surface portion 224 and outside surface portion 118 such that metal-detectable inserts 200, 200' and 200" are captured within lens body 100 between the inside and outside surface portions thereof.

In the arrangement shown in FIG. 5, inside surface portion 220 of component body 206 and outside surface portion 222 of the component body are respectively exposed on or along inside and outside surface portions 116 and 118 of lens body 100. In some cases, surface portions 220 and/or 222 can have a shape and/or contour that approximately matches that of inside surface portion 116 and/or outside surface portion 118, respectively. In other cases, the inside surface portion and/or the outside surface portion of component body 206 can be approximately planar, recessed into and/or projecting outwardly beyond outside surface portions 118, such as are collectively represented in FIG. 5 by dashed lines 228 and 230, respectively. It will be appreciated that in such an arrangement, the space or channel formed between intermediate surface portions 224 in FIG. 5 will be disposed between inside and outside surface portions 116 and 118. A portion 132 of lens body 100 is disposed within the channel between the intermediate surface portion thereby capturing metal-detectable components 200, 200' and 200" within lens body 100 between the inside and outside surface portions thereof. For example, in some cases, the metal-detectable components can have an approximately circular shape (e.g., in FIG. 3) with the space or channel in component bodies 206 taking the form of an annular groove. It will be appreciated, however, that other configurations and/or arrangements can alternately be used.

As still another non-limiting example, a protective eyewear lens assembly AS4 in accordance with the subject matter of the present disclosure is shown in FIGS. 6-12 as including lens body 100, as shown and described above, and one or more metal-detectable components 200''' that are at least partially embedded, encased and/or otherwise captured on, along and/or within lens body 100. As with the arrangements shown and described in FIGS. 1-5 in connection with metal-detectable components 200, 200' and 200", metal-detectable components 200''' include one or more portions that are positioned adjacent or otherwise extend at least partially along body periphery portion 112 and/or any one or more of segments 112A-D thereof. Additionally, as with the arrangements shown and described in FIGS. 1-5 in connection with metal-detectable components 200, 200' and 200", metal-detectable components 200''' are, in a preferred arrangement, permanently (i.e., inseparable without damage, destruction or material alteration of at least one of the component parts) enclosed or otherwise encapsulated within lens body 100. Metal-detectable components 200''' differ from metal-detectable components 200, 200' and 200", in that metal-detectable components 200''' are, in a preferred arrangement, substantially entirely encased or otherwise enclosed within lens body 100, such that no substantial portion of metal-detectable components 200''' are exposed to an external atmosphere). Whereas, metal-detectable components 200, 200' and 200" are described as having one or more surface portions that can be exposed outwardly of or otherwise along lens body 100.

Figure 6:
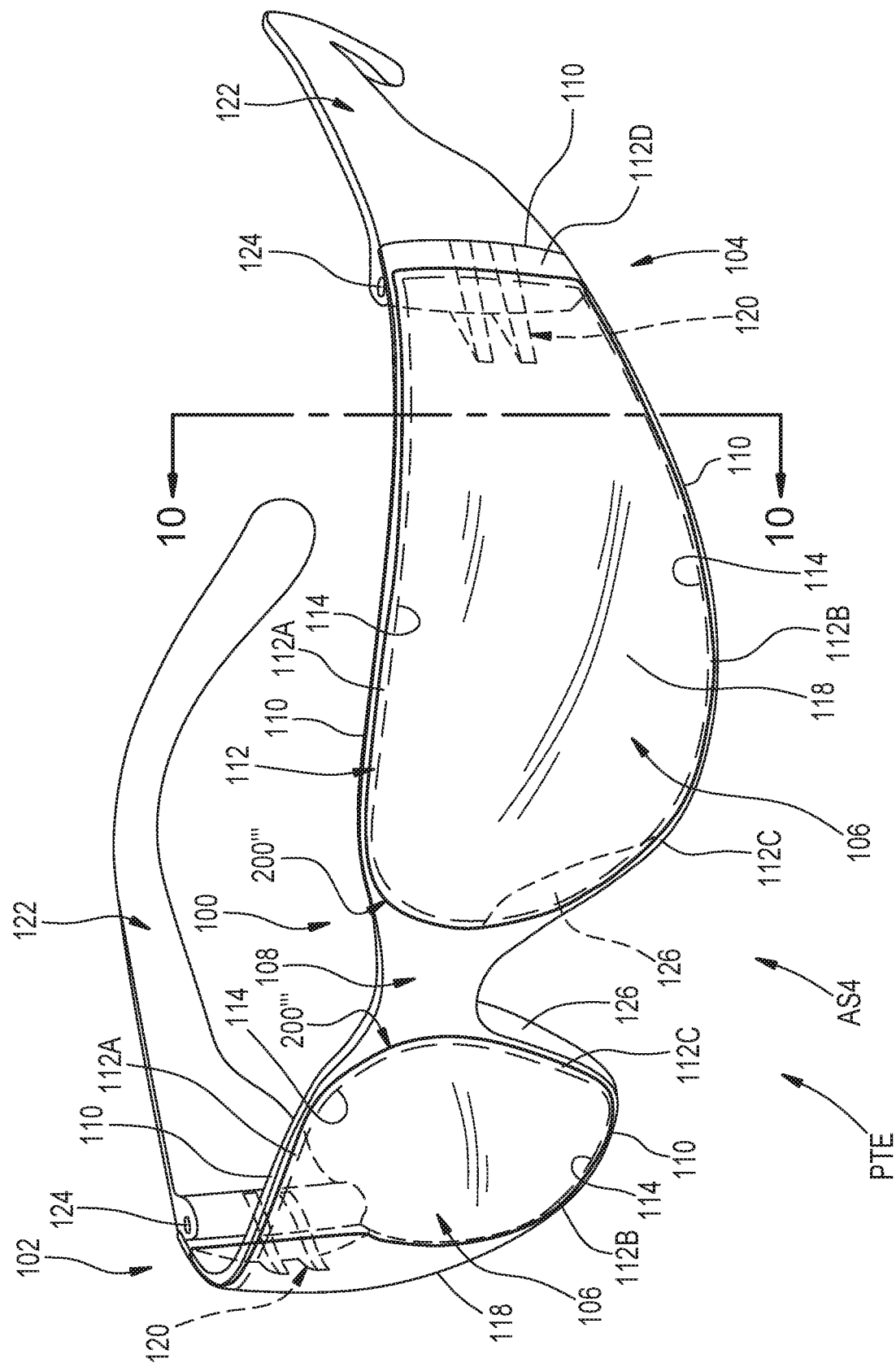
FIG. 6 is a top perspective view of yet another example of protective eyewear with a lens assembly in accordance with the subject matter of the present disclosure.

As discussed above, it will be appreciated that the one or more metal-detectable components can be of any suitable size, shape, configuration and/or arrangement, and can be formed from any suitable combination of one or more metal-detectable materials (e.g., a metal material and/or a metal-infused polymeric material). Metal-detectable components 200''' are shown in FIGS. 6-9 as being disposed on or along at least a part of body periphery portion 112 (e.g., along at least one or more of segments 112A, 112B, 112C and/or 112D). For example, as shown in FIG. 6, metal-detectable components 200''' can include a length of metal-detectable material extending along and around each of optically-transparent portions 106, such as along, through or otherwise within a combination of segments 112A-D of body periphery portion 112, for example. In some cases, metal-detectable components 200''' can extend substantially-entirely around the optically-transparent portion, such as in a continuous loop of metal-detectable material or in a discontinuous loop of material with opposing ends. In some cases, the opposing ends can be coextensive with one another (e.g., overlap). In other cases, the opposing ends can be disposed in spaced relation to one another (e.g., with a gap therebetween). In such a construction, should lens assembly AS4 be separated into two pieces, such due to a disconnection along bridge portion 108, for example, each of the two pieces will include one of metal-detectable components 200'''.

Figure 7:
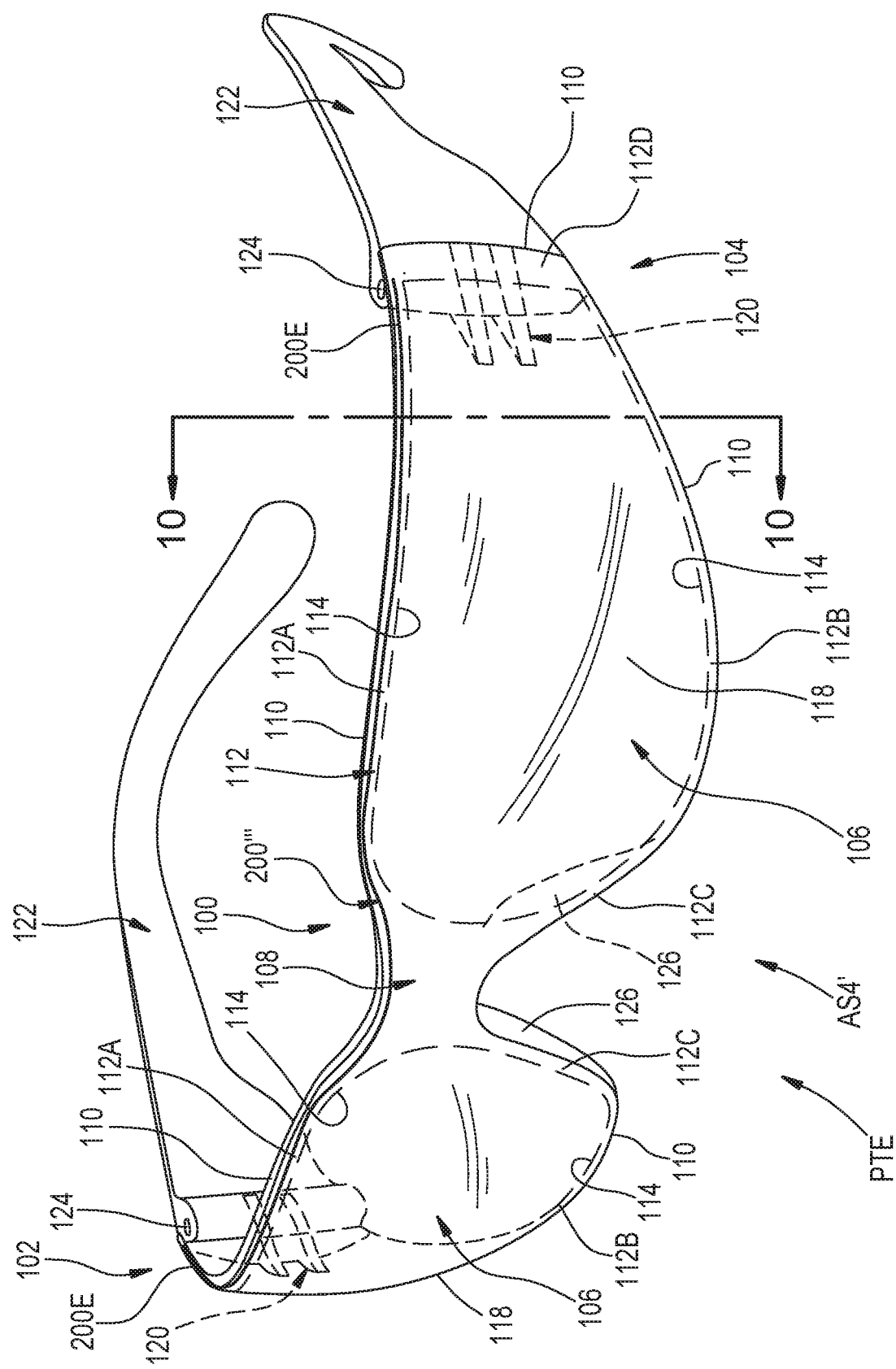
FIG. 7 is a top perspective view of yet a further example of protective eyewear with a lens assembly in accordance with the subject matter of the present disclosure.

An alternate construction of a protective eyewear lens assembly AS4' is shown in FIG. 7, which differs from protective eyewear lens assembly AS4 in FIG. 6 at least in that metal-detectable component 200''' in FIG. 7 extends lengthwise between opposing ends 200E. Metal-detectable component 200''' is shown in FIG. 7 as having one of ends 200E disposed along end 102 of lens body 100 and the other of ends 200E disposed along end 104 of the lens body. In such an arrangement, a single metal-detectable component can extend lengthwise extending along or otherwise across one of segments 112A of body periphery portion 112 disposed along an upper portion of the outer peripheral edge, along or otherwise across bridge portion 108, and then along or otherwise across the other one of segments 112A. In this manner, a substantially continuous length of magnetically-detectable material can extend across lens body 100 from end 102 to end 104.

Figure 8:
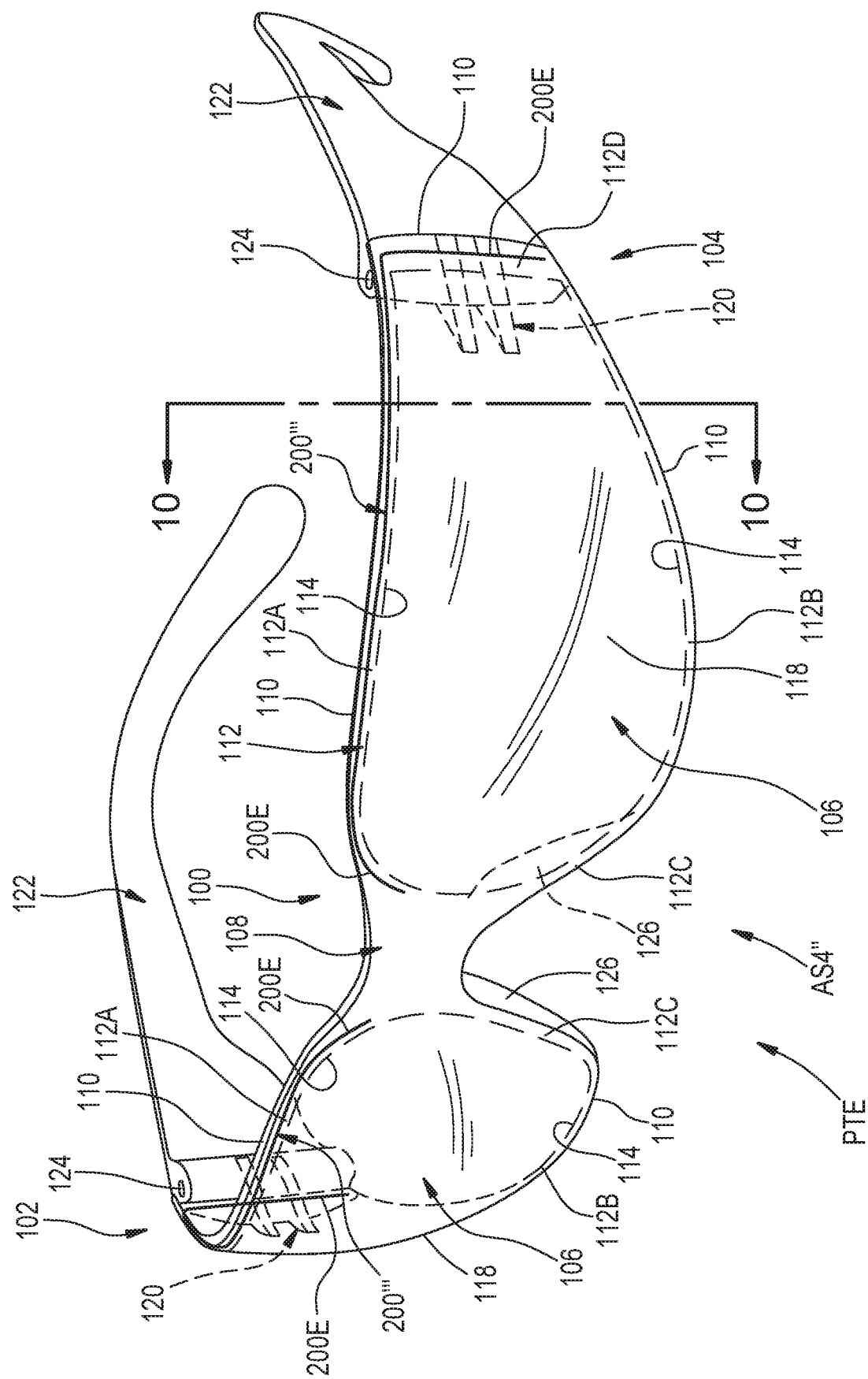
FIG. 8 is a top perspective view of still another example of protective eyewear with a lens assembly in accordance with the subject matter of the present disclosure.

Another alternate construction of a protective eyewear lens assembly AS4" is shown in FIG. 8, which differs from protective eyewear lens assembly AS4' in FIG. 7 at least in that metal-detectable component 200''' in FIG. 7 includes a single component extending lengthwise between opposing ends 200E. In the alternate construction shown in FIG. 8, a plurality of metal-detectable components 200''' are encased or otherwise enclosed within lens body 100 with each of the metal-detectable components extending between opposing ends 200E. One of the plurality of metal-detectable components is disposed along one of segments 112A with another of the plurality of metal-detectable components disposed along the other of segments 112A. Additionally, or in the alternative, one of the metal-detectable components can extend along segment 112D on end 102 and another of the metal-detectable components can extend along segment 112D on end 104. In some cases, a single elongated length of metal-detectable material can extend along two or more segments of body periphery portion 112 (e.g., along any combination of two or more of segments 112A-D) on a given side of bridge portion 108, such as along segments 112A and 112D, as shown in FIG. 8, for example. In other cases, two or more separate elongated lengths of metal-detectable material can extend along one or more segments of body periphery portion 112 (e.g., along any combination of two or more of segments 112A-D) on a given side of bridge portion 108. It will be appreciated that any and all of such combinations and configurations are intended to find support in the subject application. Extending ends 200E of each one of metal-detectable components 200''' are disposed toward one another adjacent bridge portion 108 and away from one another adjacent ends 102 and 104 of lens body 100.

Figure 9:
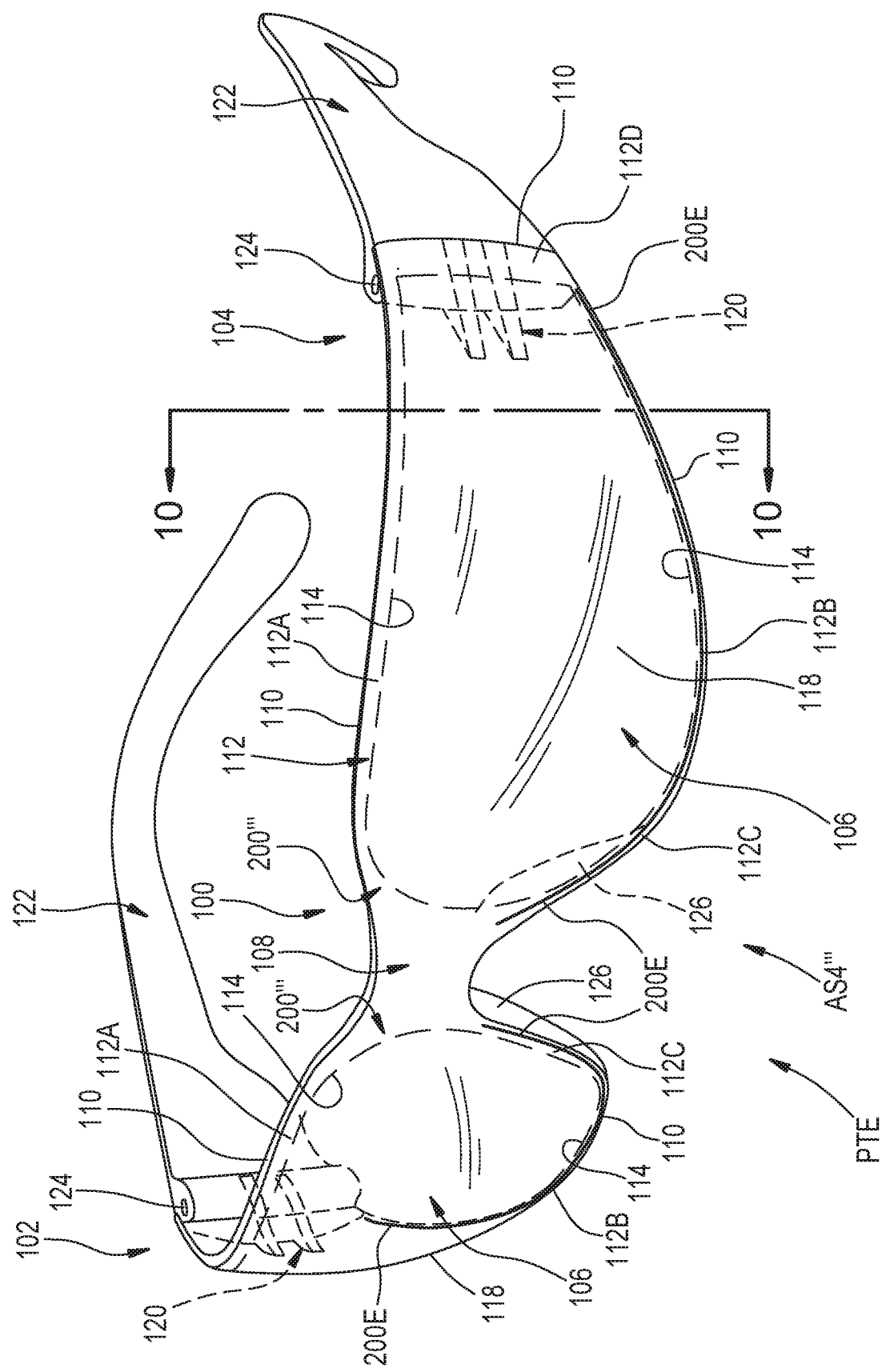
FIG. 9 is a top perspective view of still a further example of protective eyewear with a lens assembly in accordance with the subject matter of the present disclosure.

Still another alternate construction of a protective eyewear lens assembly AS4''' is shown in FIG. 9, which differs from protective eyewear lens assembly AS4" in FIG. 8 at least in that metal-detectable component 200''' in FIG. 8 includes metal-detectable components extending on or along segments 112A and/or 112D. In the alternate construction shown in FIG. 9, a plurality of metal-detectable components 200''' are encased or otherwise enclosed within lens body 100 with each of the metal-detectable components extending between opposing ends 200E. One of the plurality of metal-detectable components is disposed along one of segments 112B with another of the plurality of metal-detectable components disposed along the other of segments 112B. Additionally, or in the alternative, one of the metal-detectable components can extend along segment 112C adjacent bridge portion 108 from a direction toward end 102 and another of the metal-detectable components can extend along segment 112C adjacent bridge portion 108 from toward end 104. As discussed above, in some cases, a single elongated length of metal-detectable material can extend along two or more segments of body periphery portion 112 (e.g., along any combination of two or more of segments 112A-D) on a given side of bridge portion 108, such as along segments 112B and 112C, as shown in FIG. 9, for example. In other cases, two or more separate elongated lengths of metal-detectable material can extend along one or more segments of body periphery portion 112 (e.g., along any combination of two or more of segments 112A-D) on a given side of bridge portion 108. Again, it will be appreciated that any and all of such combinations and configurations are intended to find support in the subject application.

Figure 10:
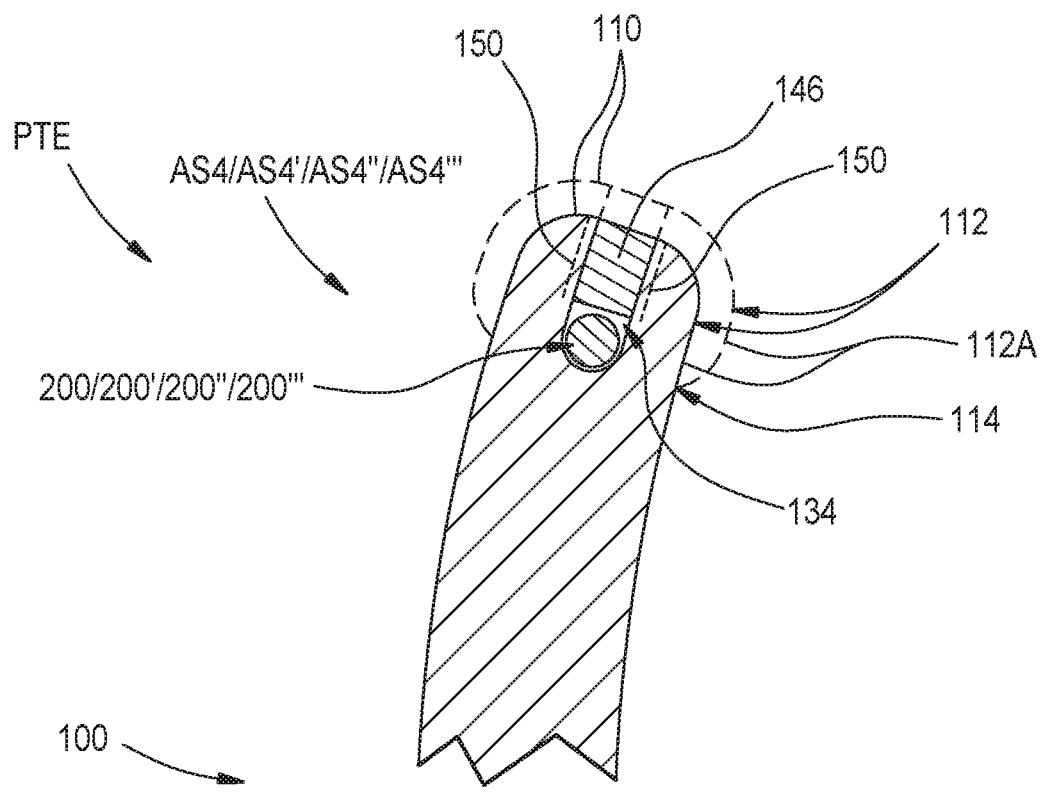
FIG. 10 is a cross-sectional side view of the exemplary assembly shown in at least FIGS. 1, 2, 4 and 6-9 taken from along line 10-10 in FIG. 6.
Figure 10:
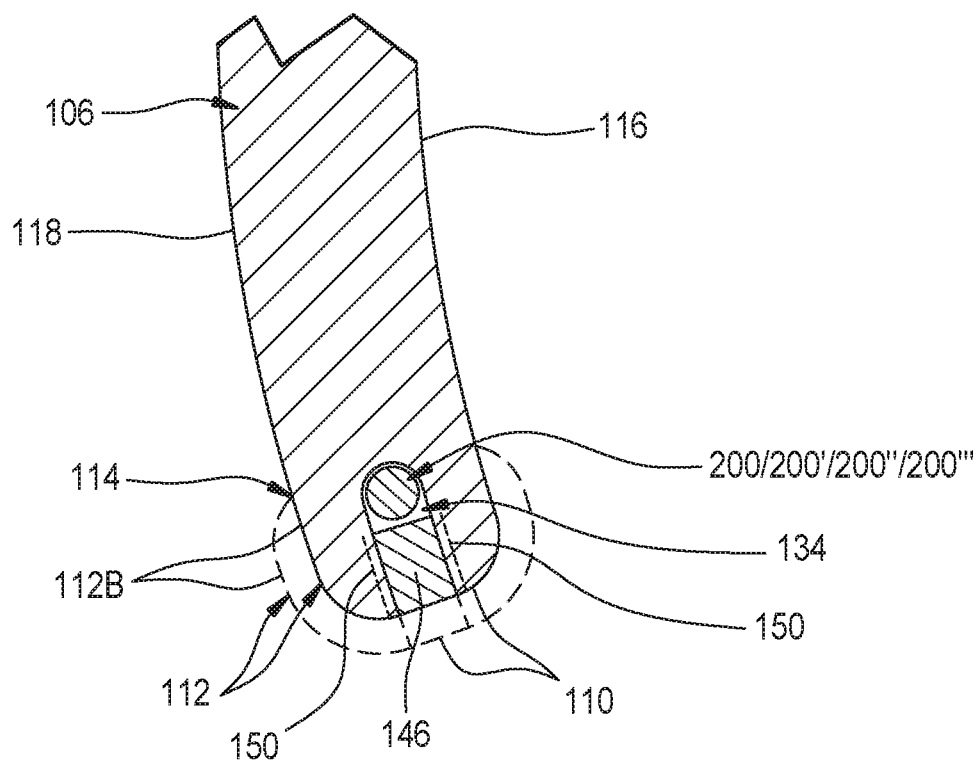

It will be appreciated that protective eyewear lens assemblies in accordance with the subject matter of the present disclosure can be produced using any suitable combination of one or more manufacturing processes and/or techniques. As one non-limiting example, lens bodies 100 can include one or more grooves, slots and/or other cavities extending into the polymeric material of the lens body and into which one or more metal-detectable components can be permanently embedded, encased, encapsulated and/or otherwise captured. It will be appreciated that the one or more grooves, slots and/or other cavities can be formed or otherwise provided from on or along any one or more surfaces and/or portions of lens body 100, such as from on or along any one or more of optically-transparent portion 106, bridge portion 108, body periphery portion 112, the additional volume of material disposed outwardly of demarcation line 114, inside surface portions 116 and/or outside surface portions 118, for example. In the exemplary arrangement, shown in FIGS. 10 and 11, for example, lens body 100 can include one or more grooves, slots and/or other cavities, which are collectively represented in FIGS. 10 and 11 by a groove 134 that extends into lens body 100 from along body periphery portion 110. Groove 134 includes an end surface portion 136 disposed inwardly of body periphery portion 110 along which an open end 138 of the groove is formed. Groove 134 is also at least partially defined by a groove side surface portion 140 disposed toward inside surface portion 116 and a groove side surface portion 142 disposed toward outside surface portion 118 and in facing relation to groove side surface portion 140. It will be appreciated that metal-detectable components 200, 200', 200'' and/or 200''' are shown in FIG. 10 as being disposed along segments 112A and 112B of body periphery portion 112, but that such a configuration is merely exemplary and that any other configuration and/or arrangement could alternately be used, such as have been shown and described herein, for example.

Figure 11:
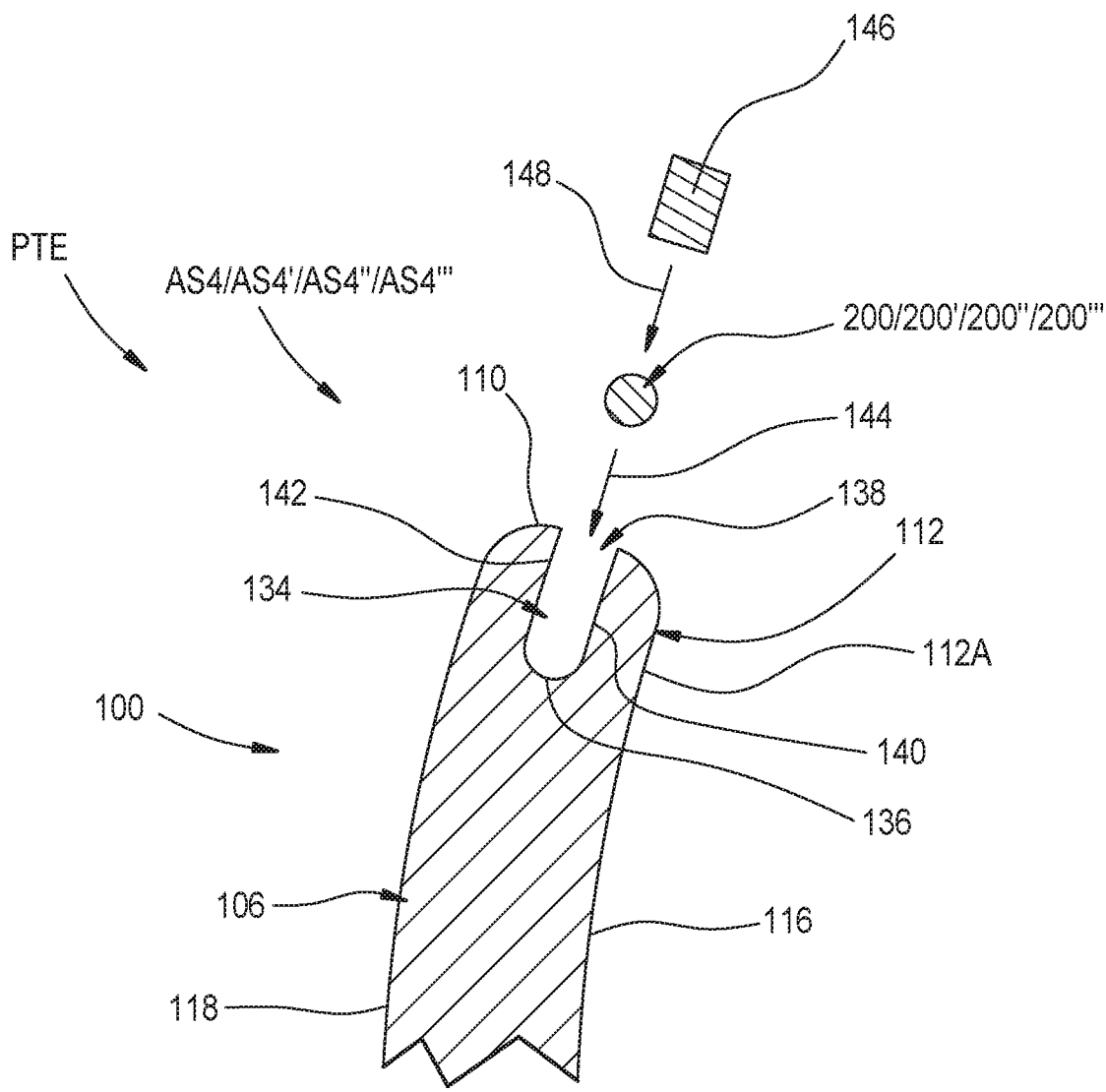
FIG. 11 illustrates components of an exemplary lens assembly, such as is shown in at least FIGS. 1, 2, 4 and 6-9, prior to assembly and illustrating a method of manufacture.

The one or more grooves, slots and/or other cavities within which one or more of metal-detectable components 200, 200', 200'' and/or 200''' can be permanently embedded, encased, encapsulated and/or otherwise captured extend on, along and/or otherwise around one or more portions of the lens body. In some cases, the one or more grooves, slots and/or other cavities can have an elongated length, such as to receive or otherwise accommodate one or more portions of any one or more of metal-detectable components 200' and/or 200''', for example. As shown in FIG. 11, upon forming or otherwise providing one or more of grooves 134 on or along lens body 110, one or more of metal-detectable components 200, 200', 200'' and/or 200''' can be positioned within corresponding ones of the one or more grooves, as is represented in FIG. 11 by arrow 144. One or more cover wall portions 146, which can be formed from a second quantity of polymeric material, can be provided that is dimensioned to extend across and at least partially cover open end 138 of groove 134 such that the one or more metal-detectable components are permanently embedded, encased, encapsulated and/or otherwise captured within one or more of the one or more grooves, slots and/or other cavities. It will be appreciated that cover wall portions 146 can be secured to lens body 100 in any suitable manner. As one non-limiting example, cover wall portion 146 can be positioned within open end 138 of groove 134, as is represented in FIG. 11 by arrow 148, and secured to lens body 100 by way of a flowed material joint, such as is represented by dashed lines 150 in FIG. 10, for example.

Figure 12:
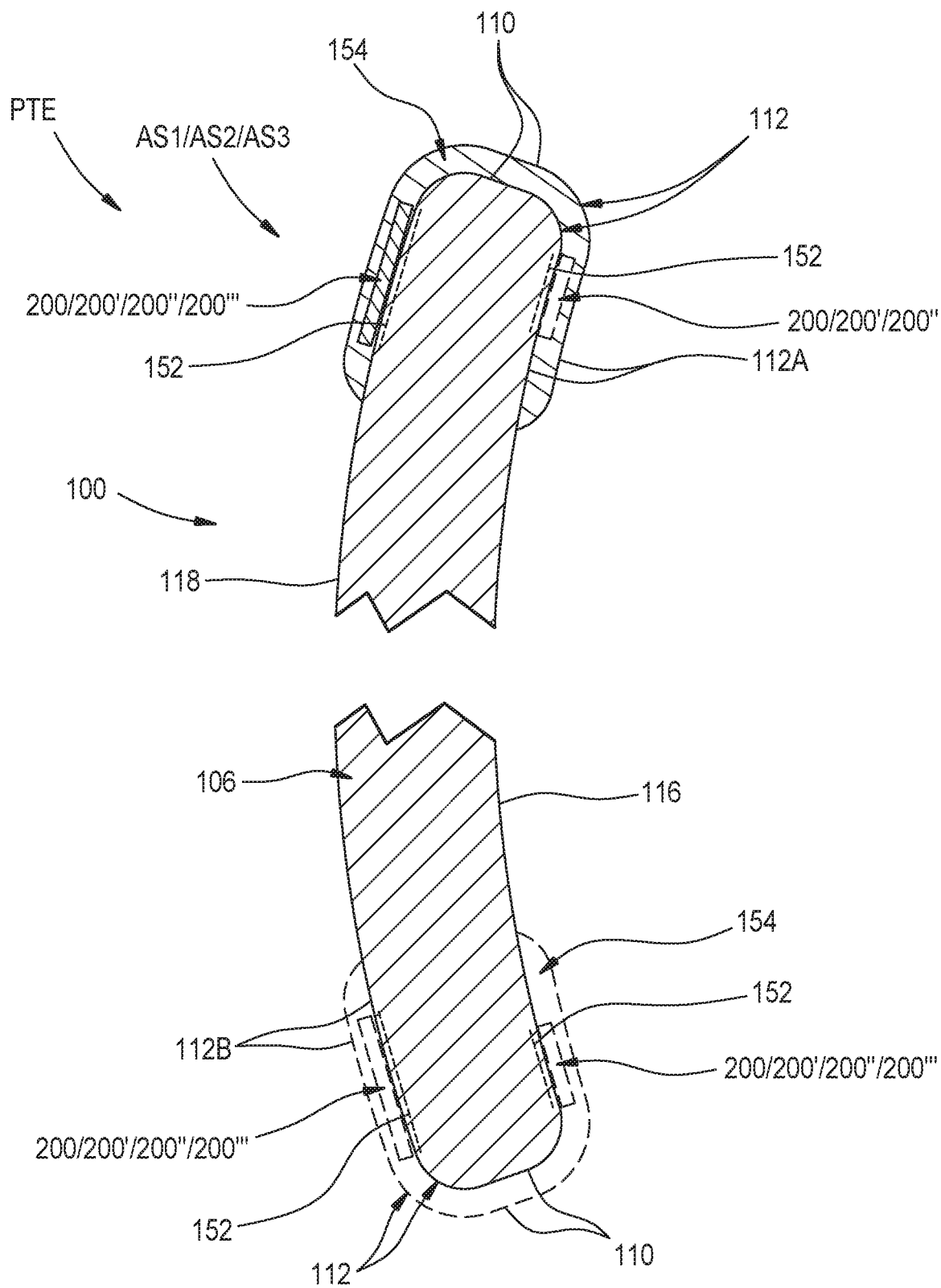
FIG. 12 is a cross-sectional side view of an alternate construction of the exemplary lens assemblies shown in FIGS. 1, 2, 4 and 6-9.
Figure 13:
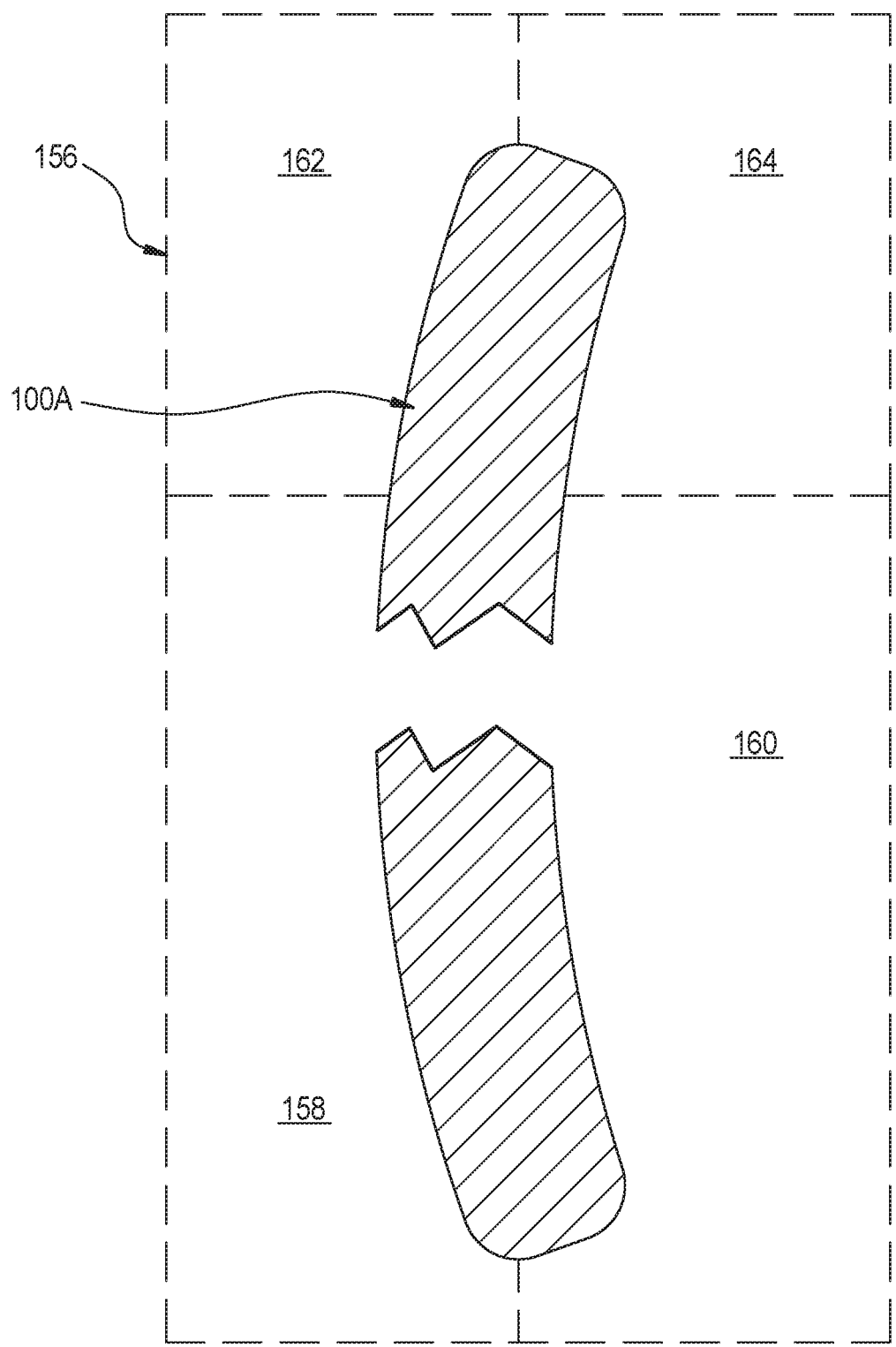
FIG. 13 is a schematic representation of a lens component of an exemplary lens assembly in accordance with the subject matter of the present disclosure manufactured within a first mold assembly.
Figure 14:
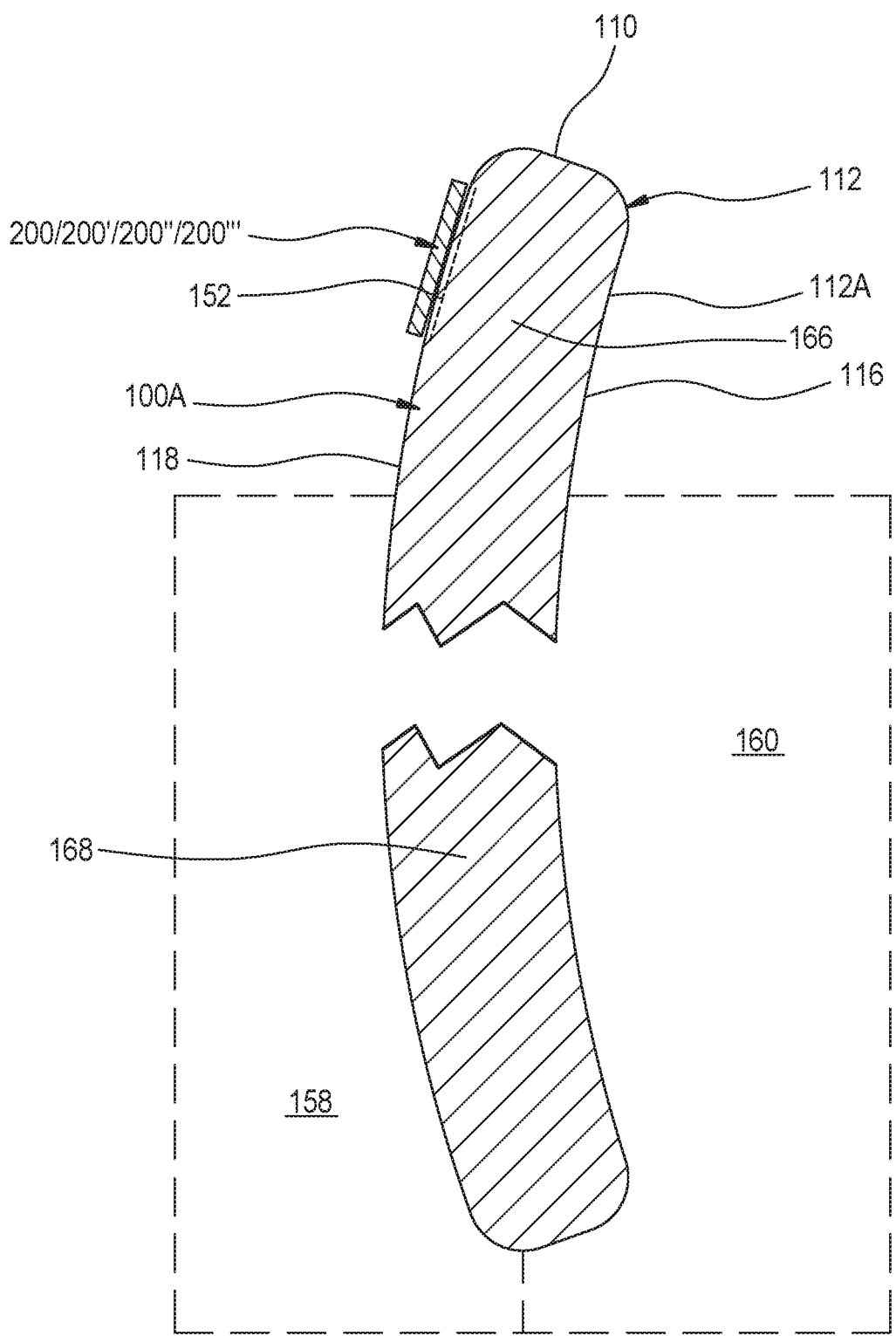
FIG. 14 is a schematic representation of the exemplary lens component in FIG. 13 with a portion of the first mold assembly removed and a portion of the exemplary lens component retained in the remainder of the first mold assembly as well as a detectable component positioned along an exposed portion of the exemplary lens component.
Figure 15:
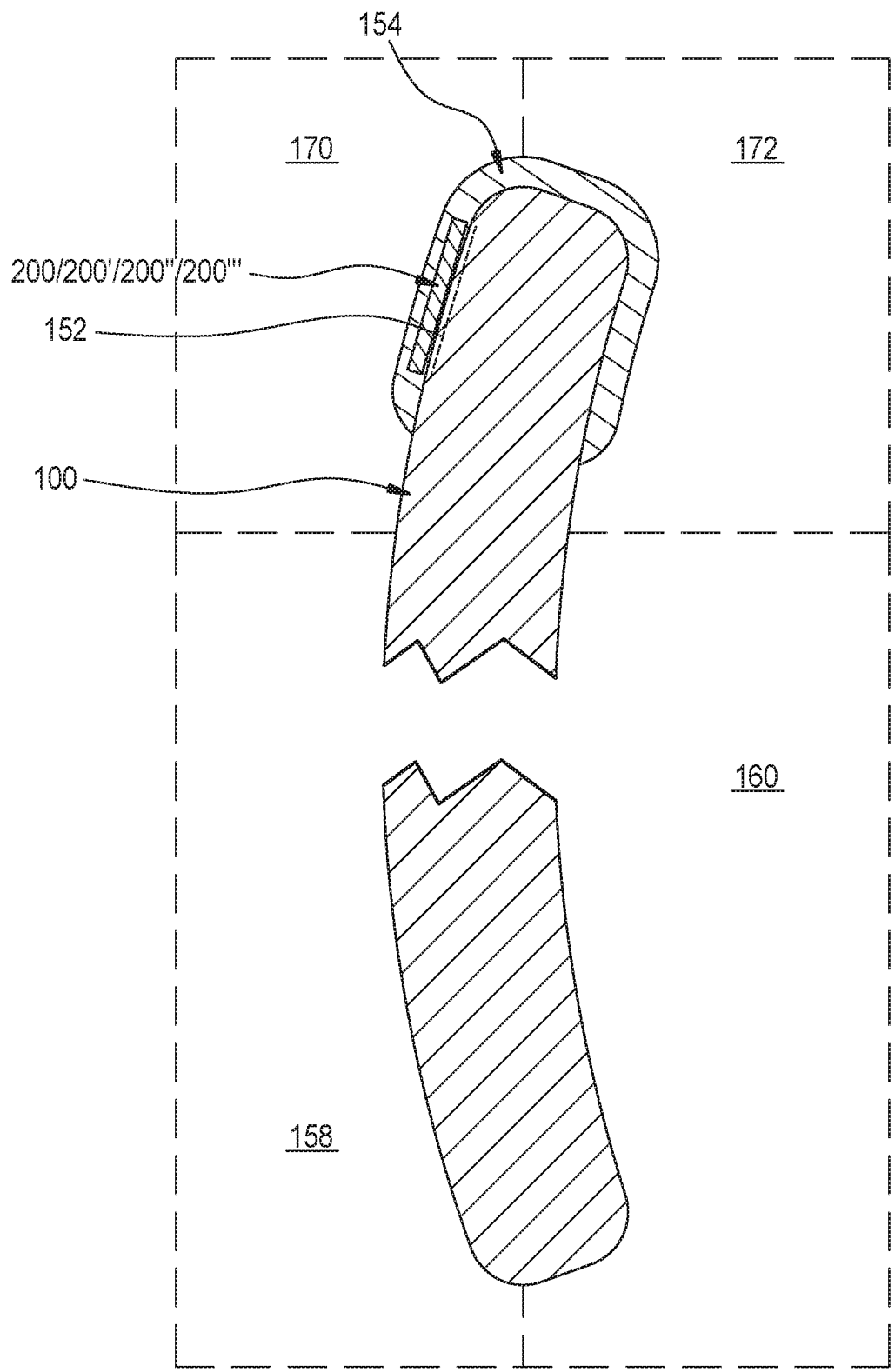
FIG. 15 is a schematic representation of the exposed portion of the component of the exemplary lens component and the detectable component of FIG. 14 positioned within a second mold assembly and a further component of the exemplary eyewear formed in situ to encase at least the detectable component.
Figure 16:
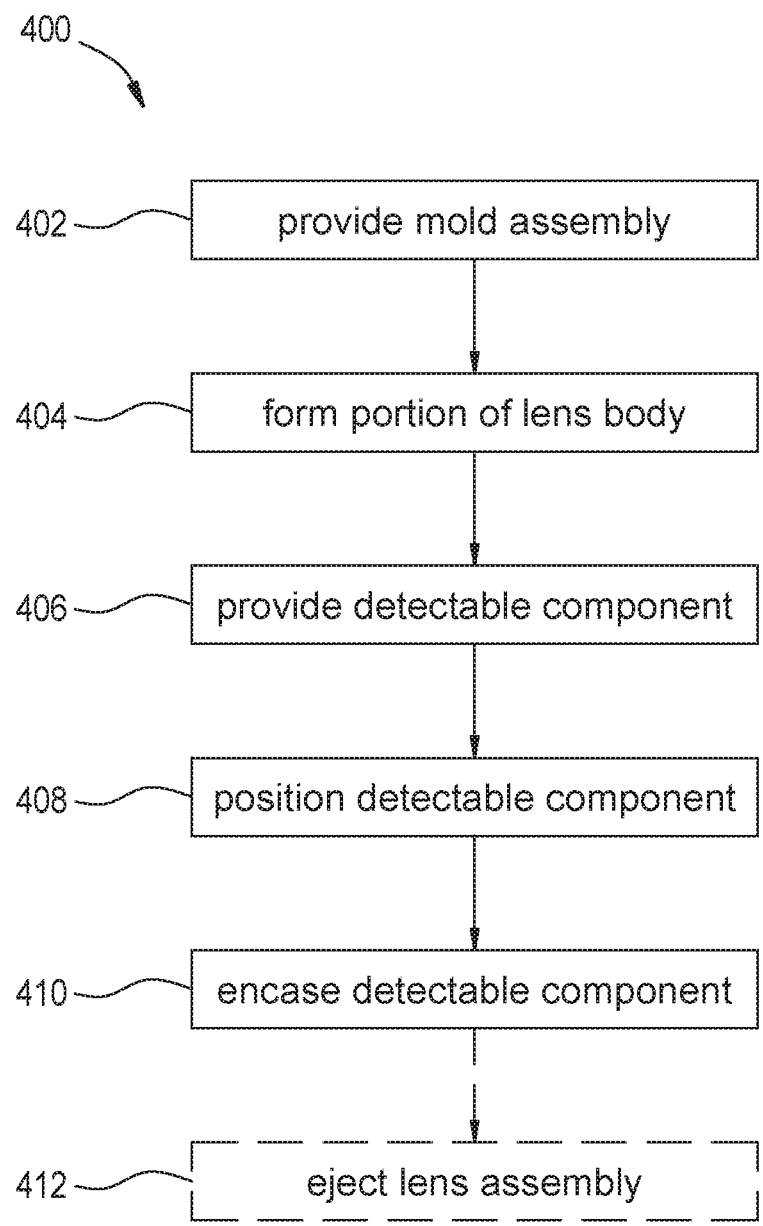
FIG. 16 is a graphical representation of one example of a method of manufacturing metal-detectable protective eyewear in accordance with the subject matter of the present disclosure.

FIGS. 12-15 illustrate another, non-limiting example of one or more manufacturing processes and/or techniques by which protective eyewear lens assemblies in accordance with the subject matter of the present disclosure can be produced. As shown therein, one or more of metal-detectable components 200, 200', 200'' and/or 200''' are positioned on or along one or more of inside and outside surface portions 116 and/or 118. In a preferred arrangement, such one or more of metal-detectable components 200, 200', 200'' and/or 200''' can be secured on or along the corresponding one or more of the inside and/or outside surface portions by way of an adhesive and/or flowed-material joint, such as is represented in FIG. 12 by dashed lines 152, for example. In accordance with the subject matter of the present disclosure, the one or more metal-detectable components are, preferably, permanently embedded, encased, encapsulated and/or otherwise captured within the protective eyewear lens assembly such that the one or more metal-detectable components cannot be separated or otherwise disassociated from the lens body without damage, destruction or material alteration of at least one of the component parts of the lens assembly. As one non-limiting example, metal-detectable components 200, 200', 200'' and/or 200''' are shown in FIGS. 16 and 15 as being permanently embedded, encased, encapsulated and/or otherwise captured within cover wall portion 154, which extends on and/or along one or more surfaces and/or portions of lens body 100, such as from on or along any one or more of optically-transparent portion 106, bridge portion 108, body periphery portion 112, inside surface portions 116 and/or outside surface portions 118, for example. As one non-limiting example, one or more metal-detectable components 200, 200', 200'' and/or 200''' are shown in FIG. 12 as being disposed along segment 112A embedded, encased, encapsulated and/or otherwise captured within cover wall portion 154. Additionally, or in the alternative, the one or more additional metal-detectable components can, optionally, be disposed on or along segment 112B of body periphery portion 112, such as is represented by the dashed-line outline thereof in FIG. 12. As such, it will be recognized and appreciated that the configurations shown and described in connection with FIGS. 12-15 are merely exemplary and that any other configuration and/or arrangement could alternately be used, such as have been shown and described herein, for example.

It will be appreciated that metal-detectable components 200, 200', 200" and/or 200''' can be permanently embedded, encased, encapsulated and/or otherwise captured within cover wall portion 154 in any suitable manner and produced using any suitable combination of one or more manufacturing processes and/or techniques. As one non-limiting example, FIGS. 13-15 illustrate manufacturing of protective eyewear lens assemblies in accordance with the subject matter of the present disclosure by forming lens body 100 in a mold assembly 156 that includes a plurality of mold sections that together at least partially define a mold cavity (not numbered), such as is shown in FIG. 13. As a non-limiting example, mold assembly is schematically illustrated as including mold sections 158, 160, 162 and 164. It will be appreciated that any combination and/or arrangement of two or more otherwise conventional mold sections can be used. Once an initial lens body 100A is at least partially formed from a polymeric material, such as an optically-transparent polycarbonate material, for example, as shown in FIG. 13, one or more mold sections, such as one or more of mold sections 162 and/or 164, for example, can be removed or otherwise displaced from an assembled mold position such that a first portion 166 of initial lens body 100A is exposed while a second portion 168 of initial lens body 100A remains retained in-situ within the remaining mold sections (e.g., mold sections 158 and 160). As shown in FIG. 14, one or more metal-detectable components 200, 200', 200" and/or 200''' can be secured on or along one or more of optically-transparent portion 106, bridge portion 108, body periphery portion 112, inside surface portions 116 and/or outside surface portions 118. As shown in FIG. 15, one or more mold sections 170 and/or 172 can be introduced, such as in place of mold sections 162 and/or 164. Mold sections 166 and 168 are shown as at least partially defining an alternate portion of a mold cavity (not numbered) corresponding to the size, shape and configuration of cover wall portion 154, which can then be injected or otherwise formed, such as from a second quantity of polymeric material. Lens assembly 100 can then be ejected or otherwise removed from the mold assembly. Using an exemplary process such as the foregoing, metal-detectable components 200, 200', 200" and/or 200''' can be permanently embedded, encased, encapsulated and/or otherwise captured within cover wall portion 154. It will be appreciated, however, that other combinations of processes and/or techniques could alternately be used.

FIG. 16 graphically illustrates one example of a method 400 in accordance with the subject matter of the present disclosure of manufacturing protective eyewear, such as protective eyewear PTE, for example. As shown therein, method 400 can include providing a mold assembly that includes a mold cavity, as is represented in FIG. 16 by box 402. Method 400 can also include forming a portion of a lens body (e.g., a portion of lens body 100), as is represented in FIG. 10 by box 404, such as by introducing a first quantity of flowable polymeric material into the mold cavity. Method 400 can also include providing one or more metal-detectable components, such as any combination of one or more of metal-detectable components 200, 200', 200" and/or 200''', for example, and positioning the one or more metal-detectable components on or along the portion of the lens body, as are respectively represented in FIG. 16 by boxes 406 and 408. Method 400 can further include encasing the one or more metal-detectable components, as is represented in FIG. 10 by box 410. Method 400 can, optionally, include ejecting or otherwise removing the lens body together with the one or more metal-detectable components from the mold assembly as lens assemblies (e.g., protective eyewear lens assemblies AS1, AS2, AS3, AS4, AS4', AS4" and/or AS4'''), as is represented in FIG. 16 by box 412.

It will be appreciated that the lens bodies of protective eyewear lens assemblies AS1, AS2, AS3, AS4, AS4', AS4" and/or AS4''' can be formed from any suitable material or combination of materials. As one example, optically-transparent portions 106 of lens bodies 100 can be formed from an optically-clear (tinted or untinted, and coated or uncoated) polymeric material, such as a polycarbonate, for example. In accordance with the subject matter of the present disclosure, metal-detectable components, such as one or more of metal-detectable components 200, 200', 200" and/or 200''' can, in some cases, be at least partially formed from a polymeric material that has metal-detectable (e.g., conductively-detectable and/or magnetically-detectable) particles distributed substantially-evenly throughout the material. Additionally, or in the alternative, metal-detectable components, such as one or more of metal-detectable components 200, 200', 200" and/or 200''' can, in some cases, be at least partially formed from metallic material, such as steel, copper or brass that is metal-detectable (e.g., conductively-detectable and/or magnetically-detectable) and which can be coated or uncoated. It will be appreciated that such metal-detectable materials can be of any suitable size, shape, configuration and/or arrangement, such as thin sheets or foils, wire loops, wire segments and/or other bodies in regular (e.g., round, polygonal) and/or irregular shapes and/or cross-sections. Additionally, it will be appreciated that such metal-detectable materials can be formed in any suitable manner and/or by any combination of one or more processes, such as drawing, forging, stamping, molding, casting, cutting and/or milling, for example. In a preferred arrangement, optically-transparent portions 106 together with any additional portions (e.g., bridge portions 108) and/or components (e.g., temples 122) form the structural features of the protective eyewear with the one or more of metal-detectable components 200, 200', 200" and/or 200''', preferably, forming non-structural features of the protective eyewear assemblies.

Additionally, it will be appreciated that metal-detectable components can be formed from any suitable material or combination of materials, such as one or more materials that can be detected or are detectable using conventional systems, equipment and/or techniques for identifying foreign material in manufacturing and/or food production processes (e.g., magnetically-detectable and/or otherwise metal-detectable). Additionally, conventional systems employ widely adopted test standards associated with the use and operation of conventional systems. As non-limiting examples, one or more of metal-detectable components 200, 200', 200" and/or 200''' could be at least partially formed from a metal material and/or a metal-infused polymeric material having a metal detectability equivalent to at least a 3 mm metal sphere. In some cases, the one or more metal-detectable components can have a collective, total metal detectability equivalent to at least a 3 mm metal sphere. In other cases, each of the one or more metal-detectable components can have a metal detectability equivalent to at least a 3 mm metal sphere. In preferred arrangement, the one or more metal-detectable components can have a collective, total metal detectability equivalent to at least a 2 mm metal sphere. In some such cases, each of the one or more metal-detectable components can have a metal detectability equivalent to at least a 2 mm metal sphere. In a more preferred arrangement, the one or more metal-detectable components can have a collective, total metal detectability equivalent to at least a 1 mm metal sphere. In other cases, each of the one or more metal-detectable components can have a metal detectability equivalent to at least a 1 mm metal sphere.

As used herein with reference to certain features, elements, components and/or structures, numerical ordinals (e.g., first, second, third, fourth, etc.) may be used to denote different singles of a plurality or otherwise identify certain features, elements, components and/or structures, and do not imply any order or sequence unless specifically defined by the claim language.

Furthermore, terms such as "transverse" and the like, if used herein, are to be broadly interpreted to include a wide range of relative angular orientations that include, but are not limited to, an approximately perpendicular angular orientation. Also, terms such as "circumferential," "circumferentially," and the like, if used herein, are to be broadly interpreted and can include, but are not limited to circular shapes and/or configurations. In this regard, terms such as "circumferential," "circumferentially," and the like, can be synonymous with terms such as "peripheral," "peripherally," and the like.

Further still, the phrase "flowed-material joint" and the like, if used herein, are to be interpreted to include any joint or connection in which a liquid or otherwise flowable material (e.g., a melted metal or combination of melted metals) is deposited or otherwise presented between adjacent component parts and operative to form a fixed and substantially fluid-tight connection therebetween. Examples of processes that can be used to form such a flowed-material joint include, without limitation, welding processes, brazing processes and soldering processes. In such cases, one or more metal materials and/or alloys can be used to form such a flowed-material joint, in addition to any material from the component parts themselves. Another example of a process that can be used to form a flowed-material joint includes applying, depositing or otherwise presenting an adhesive between adjacent component parts that is operative to form a fixed and substantially fluid-tight connection therebetween. In such case, it will be appreciated that any suitable adhesive material or combination of materials can be used, such as one-part and/or two-part epoxies, for example.

It will be recognized that numerous different features and/or components are presented in the embodiments shown and described herein, and that no one embodiment may be specifically shown and described as including all such features and components. As such, it is to be understood that the subject matter of the present disclosure is intended to encompass any and all combinations of the different features and components that are shown and described herein, and, without limitation, that any suitable arrangement of features and components, in any combination, can be used. Thus, it is to be distinctly understood claims directed to any such combination of features and/or components, whether or not specifically embodied herein, are intended to find support in the present disclosure. To aid the Patent Office and any readers of this application and any resulting patent in interpreting the claims appended hereto, Applicant does not intend any of the appended claims or any claim elements to invoke 35 U.S.C. 112(f) unless the words "means for" or "step for" are explicitly used in the particular claim.

Thus, while the subject matter of the present disclosure has been described with reference to the foregoing embodiments and considerable emphasis has been placed herein on the structures and structural interrelationships between the component parts of the embodiments disclosed, it will be appreciated that other embodiments can be made and that many changes can be made in the embodiments illustrated and described without departing from the principles hereof. Obviously, modifications and alterations will occur to others upon reading and understanding the preceding detailed description. Accordingly, it is to be distinctly understood that the foregoing descriptive matter is to be interpreted merely as illustrative of the subject matter of the present disclosure and not as a limitation. As such, it is intended that the subject matter of the present disclosure be construed as including all such modifications and alterations.

The invention claimed is:

1. A protective eyewear lens assembly comprising:
a lens body at least partially formed from a first quantity of polymeric material, said lens body having a width and extending widthwise between a first end and a second end opposite said first end, said lens body including a first optically-transparent portion disposed toward said first end, a second optically-transparent portion disposed toward said second end, a first hinge connection disposed along said first end and a second hinge connection disposed along said second end with said first and second optically-transparent portions and said first and second hinge connections unitarily formed from said first quantity of polymeric material, and said lens body including an outer peripheral edge with an elongated groove extending into said lens body along said outer peripheral edge;
a metal-detectable component formed from an elongated length of metal-detectable material and extending lengthwise between first and second component ends disposed within said elongated groove of said lens body; and,
an elongated cover wall formed from a second quantity of polymeric material that is separate from said first quantity of polymeric material, said elongated cover wall disposed within and extending along said elongated groove, said elongated cover wall permanently attached to said lens body such that said metal-detectable component is permanently and substantially-entirely encased in said lens body within said elongated groove by said elongated cover wall.

2. A protective eyewear lens assembly according to claim 1, wherein said metal-detectable component is one of a plurality of metal-detectable components permanently encased along said lens body with said plurality of metal-detectable components having a total metal detectability equivalent to at least a 1 mm ferrous sphere.

3. A protective eyewear lens assembly according to claim 2, wherein each of said plurality of metal-detectable components has a metal detectability equivalent to at least a 1 mm ferrous sphere.

4. A protective eyewear lens assembly according to claim 1, wherein said metal-detectable component is one of a plurality of metal-detectable components with each of said plurality of metal-detectable components permanently encased on said lens body.

5. A protective eyewear lens assembly according to claim 4, wherein said elongated cover wall is a first elongated cover wall, one of said plurality of metal-detectable components is permanently encased on said lens body by said first elongated cover wall and another of said plurality of metal-detectable components is permanently encased on said lens body by a second elongated cover wall formed from a third quantity of polymeric material that is separate from said first and second quantities of polymeric material.

6. A protective eyewear lens assembly according to claim 1, wherein said lens body includes a bridge portion disposed between said first and second optically-transparent portions, and said metal-detectable component is a first metal-detectable component that includes an elongated length of metal-detectable material extending between a first component end disposed along said first end of said lens body and a second component end disposed adjacent said bridge portion of said lens body with a second metal-detectable component that includes an elongated length of metal-detectable material extending between a first component end disposed along said second end of said lens body and a second component end disposed adjacent said bridge portion of said lens body opposite said second component end of said first metal-detectable component.

7. A protective eyewear lens assembly according to claim 1, wherein said lens body includes a bridge portion disposed between said first and second optically-transparent portions with said first hinge connection, said second hinge connection, said first and second optically-transparent portions and said bridge portion unitarily formed from said first quantity of polymeric material.

8. A protective eyewear lens assembly according to claim 1, wherein said lens body includes a top segment of said outer peripheral edge with at least a portion of said elongated groove extending along said top segment, and said metal-detectable components at least partially disposed within said elongated groove along said top segment.

9. A protective eyewear lens assembly according to claim 1, wherein said lens body includes a bottom segment of said outer peripheral edge with at least a portion of said elongated groove extending along said bottom segment, and said metal-detectable components at least partially disposed within said elongated groove along said bottom segment.

10. A protective eyewear lens assembly according to claim 1, wherein said lens body includes an inside segment of said outer peripheral edge with at least a portion of said elongated groove extending along said inside segment, and said metal-detectable component at least partially disposed within said elongated groove along said inside segment.

11. A protective eyewear lens assembly according to claim 1, wherein said lens body includes an outside segment of said outer peripheral edge with at least a portion of said elongated groove extending along said outside segment, and said metal-detectable components at least partially disposed within said elongated groove along said outside segment.

12. A protective eyewear lens assembly according to claim 1, wherein said metal-detectable component extends in a loop around at least a portion of said outer peripheral edge.

13. A protective eyewear assembly comprising:
a lens assembly including:
a lens body at least partially formed from a first quantity of polymeric material, said lens body having a body width, a body height and a body thickness, said lens body extending in a widthwise direction between a first body end and a second body end opposite said first body end, said lens body including a first body side surface dimensioned to face toward an associated wearer and a second body side surface portion facing opposite said first side surface portion such that said body thickness is defined therebetween, said lens body including first and second hinge connections with said first hinge connection disposed along said first body end and said second hinge connection disposed along said second body end, a first optically-transparent portion disposed toward said first body end, a second optically-transparent portion disposed toward said second body end and a bridge portion disposed between and operatively interconnecting said first and second optically-transparent portions, and with said first hinge connection, said second hinge connection, said first and second optically-transparent portions and said bridge portion unitarily formed from said first polymeric material, and said lens body including an outer peripheral edge with an elongated groove extending into said lens body along at least a portion of said outer peripheral edge;
a metal-detectable component formed from an elongated length of metal-detectable material and extending lengthwise between first and second component ends; and,
an elongated cover wall formed from a second quantity of polymeric material that is separate from said first quantity of polymeric material, said elongated cover wall disposed within and extending along said elongated groove in said widthwise direction of said lens body, said elongated cover wall permanently attached to said lens body such that said metal-detectable component is permanently and substantially-entirely encased along said lens body by said elongated cover wall;
a first temple pivotally attached to said first hinge connection of said lens body; and,
a second temple pivotally attached to said second hinge connection of said lens body.

14. A protective eyewear assembly according to claim 13, wherein said metal-detectable component is one of a plurality of metal-detectable components permanently encased along said lens body of said lens assembly and said plurality of metal-detectable components have a total metal detectability equivalent to at least a 1 mm ferrous sphere.

15. A protective eyewear assembly according to claim 13, wherein said lens body includes a top edge segment of said outer peripheral edge with at least a portion of said elongated groove extending along said top edge segment, and said metal-detectable component is at least partially disposed within said elongated groove along said top edge segment.

16. A protective eyewear assembly according to claim 13, wherein said lens body includes a bottom edge segment of said outer peripheral edge with at least a portion of said elongated groove extending along said bottom edge segment, and said metal-detectable component is at least partially disposed within said elongated groove along said bottom edge segment.

17. A protective eyewear assembly according to claim 13, wherein said lens body includes an inward edge segment of said outer peripheral edge with at least a portion of said elongated groove extending along said inward edge segment, and said metal-detectable component is at least partially disposed within said elongated groove along said inward edge segment.

18. A protective eyewear assembly according to claim 13, wherein said lens body includes an outward edge segment of said outer peripheral edge with at least a portion of said elongated groove extending along said outward edge segment, and said metal-detectable components at least partially disposed within said elongated groove along said outward edge segment.

19. A protective eyewear assembly comprising:
a lens body at least partially formed from a first quantity of polymeric material, said lens body having a width and extending widthwise between a first end and a second end opposite said first end, said lens body including a first hinge connection disposed along said first end and a second hinge connection disposed along said second end, said lens body including a first optically-transparent portion disposed toward said first end and a second optically-transparent portion disposed toward said second end, and said lens body including a bridge portion disposed between and operatively interconnecting said first and second optically-transparent portions with a first nose pad disposed along said first optically-transparent portion adjacent said bridge portion and a second nose pad disposed along said second optically-transparent portion adjacent said bridge portion, and with said first hinge connection, said second hinge connection, said first and second optically-transparent portions, said first and second nose pads and said bridge portion unitarily formed from said first polymeric material, and said lens body including an outer peripheral edge with an elongated groove extending into said lens body adjacent said outer peripheral edge, said elongated groove extending lengthwise along said outer peripheral edge such that said elongated groove includes a first elongated groove side surface, a second elongated groove side surface facing opposite said first elongated groove side surface with an elongated open end exposed along said outer peripheral edge between said first and second elongated groove side surface portions;

a metal-detectable component formed from an elongated length of metal-detectable material and disposed within said elongated groove of said lens body;

an elongated cover wall formed from a second quantity of polymeric material that is separate from said first quantity of polymeric material such that said elongated cover wall includes a first elongated end surface, a second elongated end surface facing opposite said first elongated end surface, a first elongated cover side surface and a second elongated cover side surface facing opposite said first elongated cover side surface, said elongated cover wall disposed within said elongated open end of and extending along said elongated groove, said elongated cover wall positioned within said elongated groove such that said first elongated end surface is facing said metal detectable component with said first and second elongated cover side surfaces permanently attached to said first and second elongated groove side surfaces of said lens body such that said metal-detectable component is permanently and substantially-entirely encased within said lens body by at least said elongated cover wall;

a first temple pivotally attached to said first hinge connection of said lens body; and, a second temple pivotally attached to said second hinge connection of said lens body.

20. A protective eyewear assembly according to claim 19, wherein said metal-detectable component is one of a plurality of metal-detectable components permanently encased along said lens body of said lens assembly and said plurality of metal-detectable components have a total metal detectability equivalent to at least a 1 mm ferrous sphere.

* * * * *